(12) United States Patent
Mootien et al.

(10) Patent No.: US 9,788,862 B2
(45) Date of Patent: Oct. 17, 2017

(54) SACRAL FIXATION SYSTEM

(71) Applicant: DePuy Synthes Products, Inc., Raynham, MA (US)

(72) Inventors: Azagen Mootien, Rantzwiller (FR); Alfred Niederberger, Grenches (CH); Johann Fierlbeck, Salzburg (AT); Martin Altmann, Oberdorf (CH); Martin Kaufmann, Zuchwil (CH)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/708,421

(22) Filed: May 11, 2015

(65) Prior Publication Data

US 2015/0320450 A1 Nov. 12, 2015

Related U.S. Application Data

(60) Provisional application No. 61/991,829, filed on May 12, 2014, provisional application No. 61/992,105, filed on May 12, 2014.

(51) Int. Cl.
| | |
|---|---|
| *A61B 17/04* | (2006.01) |
| *A61B 17/86* | (2006.01) |
| *A61F 2/08* | (2006.01) |
| *A61B 17/68* | (2006.01) |
| *A61B 17/70* | (2006.01) |

(Continued)

(52) U.S. Cl.
CPC ........ *A61B 17/683* (2013.01); *A61B 17/1703* (2013.01); *A61B 17/1757* (2013.01); *A61B 17/7055* (2013.01); *A61B 17/7091* (2013.01); *A61B 17/86* (2013.01); *A61B 2090/3966* (2016.02)

(58) Field of Classification Search
CPC .......... A61B 17/7055; A61B 17/7062–17/707; A61B 17/84–17/86
See application file for complete search history.

(56) References Cited

U.S. PATENT DOCUMENTS

| | | | |
|---|---|---|---|
| 2,143,922 A | 1/1939 | Longfellow | |
| 2,489,870 A * | 11/1949 | Dzus | A61B 17/683 |
| | | | 411/339 |

(Continued)

FOREIGN PATENT DOCUMENTS

| | | |
|---|---|---|
| CN | 202843773 | 4/2013 |
| DE | 202007017159 U1 | 6/2008 |

(Continued)

OTHER PUBLICATIONS

International Search Report issued in PCT/US2015/030087 dated Oct. 27, 2015, 8 pages.

(Continued)

*Primary Examiner* — Eduardo C Robert
*Assistant Examiner* — Michelle C Eckman
(74) *Attorney, Agent, or Firm* — Baker & Hostetler LLP

(57) ABSTRACT

Sacral fixation implants can include first and second implant segments. One of the first and second implant segments is received in the other of the first and second implant segments, and the first and segments can be fixed with respect to movement toward and away from each other, thereby stabilizing a sacral fracture.

17 Claims, 6 Drawing Sheets

(51) Int. Cl.
  *A61B 17/17* (2006.01)
  *A61B 90/00* (2016.01)

(56) References Cited

U.S. PATENT DOCUMENTS

| | | | |
|---|---|---|---|
| 2,511,051 A * | 6/1950 | Dzus | A61B 17/683 |
| | | | 411/338 |
| 2,586,556 A * | 2/1952 | Mullikin | B42F 13/02 |
| | | | 402/57 |
| 4,016,874 A * | 4/1977 | Maffei | A61B 17/72 |
| | | | 606/62 |
| 4,047,523 A | 9/1977 | Hall | |
| 4,409,974 A | 10/1983 | Freedland | |
| 4,530,114 A | 7/1985 | Tepic | |
| 4,569,338 A | 2/1986 | Edwards | |
| 4,590,928 A | 5/1986 | Hunt et al. | |
| 4,612,918 A * | 9/1986 | Slocum | A61B 17/7055 |
| | | | 606/279 |
| 4,640,271 A * | 2/1987 | Lower | A61B 17/8685 |
| | | | 606/105 |
| 4,858,601 A * | 8/1989 | Glisson | A61B 17/8685 |
| | | | 411/389 |
| 4,930,499 A | 6/1990 | Rowe | |
| RE33,348 E * | 9/1990 | Lower | A61B 17/8685 |
| | | | 606/304 |
| 5,000,165 A | 3/1991 | Watanabe | |
| 5,108,397 A | 4/1992 | White | |
| 5,127,912 A | 7/1992 | Ray et al. | |
| 5,129,904 A | 7/1992 | Illi | |
| 5,152,794 A | 10/1992 | Davidson | |
| 5,242,444 A * | 9/1993 | MacMillan | A61B 17/1757 |
| | | | 606/60 |
| 5,300,073 A | 4/1994 | Ray et al. | |
| 5,306,275 A | 4/1994 | Bryan | |
| 5,382,257 A | 1/1995 | Lewis et al. | |
| 5,458,599 A | 10/1995 | Adobbati | |
| 5,490,855 A * | 2/1996 | Bouraly | A61B 17/15 |
| | | | 606/82 |
| 5,515,562 A | 5/1996 | Miller et al. | |
| 5,620,445 A * | 4/1997 | Brosnahan | A61B 17/72 |
| | | | 606/62 |
| 5,797,915 A | 8/1998 | Pierson, III et al. | |
| 5,800,544 A | 9/1998 | Demopulos et al. | |
| 5,827,285 A * | 10/1998 | Bramlet | A61B 17/68 |
| | | | 411/166 |
| 5,885,294 A | 3/1999 | Pedlick et al. | |
| 5,899,901 A | 5/1999 | Middleton | |
| 5,919,194 A | 7/1999 | Anderson | |
| 5,989,252 A | 11/1999 | Fumex | |
| 5,997,538 A * | 12/1999 | Asnis | A61B 17/8625 |
| | | | 606/301 |
| 6,004,327 A * | 12/1999 | Asnis | A61B 17/8869 |
| | | | 606/104 |
| 6,010,505 A | 1/2000 | Asche et al. | |
| 6,041,485 A | 3/2000 | Pedlick et al. | |
| 6,080,192 A | 6/2000 | Demopulos et al. | |
| 6,106,556 A | 8/2000 | Demopulos et al. | |
| 6,126,660 A | 10/2000 | Dietz | |
| 6,168,631 B1 * | 1/2001 | Maxwell | A61B 17/562 |
| | | | 623/17.11 |
| 6,197,028 B1 | 3/2001 | Ray et al. | |
| 6,197,065 B1 | 3/2001 | Martin et al. | |
| 6,203,543 B1 * | 3/2001 | Glossop | A61B 17/86 |
| | | | 606/246 |
| 6,214,004 B1 | 4/2001 | Coker | |
| 6,302,887 B1 * | 10/2001 | Spranza | A61B 17/683 |
| | | | 411/338 |
| 6,319,254 B1 * | 11/2001 | Giet | A61B 17/863 |
| | | | 606/104 |
| 6,348,053 B1 | 2/2002 | Cachia | |
| 6,368,326 B1 | 4/2002 | Dakin et al. | |
| 6,508,841 B2 | 1/2003 | Martin et al. | |
| 6,520,990 B1 | 2/2003 | Ray | |
| 6,544,267 B1 | 4/2003 | Cole et al. | |
| 6,558,387 B2 | 5/2003 | Errico et al. | |
| 6,565,568 B1 | 5/2003 | Rogozinski | |
| 6,602,214 B2 | 8/2003 | Heinz et al. | |
| 6,613,059 B2 | 9/2003 | Schaller et al. | |
| 6,626,916 B1 | 9/2003 | Yeung et al. | |
| 6,648,890 B2 | 11/2003 | Culbert et al. | |
| 6,648,903 B1 | 11/2003 | Pierson, III | |
| 6,712,855 B2 | 3/2004 | Martin et al. | |
| 6,730,092 B2 | 5/2004 | Songer | |
| 6,761,722 B2 | 7/2004 | Cole et al. | |
| 7,037,308 B2 | 5/2006 | Medoff | |
| 7,153,305 B2 | 12/2006 | Johnson et al. | |
| 7,326,222 B2 | 2/2008 | Dreyfuss et al. | |
| 7,410,489 B2 | 8/2008 | Dakin et al. | |
| 7,651,528 B2 | 1/2010 | Montgomery et al. | |
| 7,670,383 B1 * | 3/2010 | Brown | A61F 2/28 |
| | | | 623/22.22 |
| 7,704,252 B2 | 4/2010 | Albertson et al. | |
| 7,722,643 B2 | 5/2010 | Schaller et al. | |
| 7,749,255 B2 | 7/2010 | Johnson et al. | |
| 7,771,426 B2 | 8/2010 | Burch et al. | |
| 7,780,707 B2 | 8/2010 | Johnson et al. | |
| 7,789,895 B2 | 9/2010 | Heinz | |
| 7,799,057 B2 | 9/2010 | Hudgins et al. | |
| 7,892,255 B2 | 2/2011 | Schaller et al. | |
| 7,938,832 B2 | 5/2011 | Culbert et al. | |
| 7,947,064 B2 | 5/2011 | Bergeron et al. | |
| 8,790,406 B1 * | 7/2014 | Smith | A61F 2/4455 |
| | | | 600/202 |
| 9,358,057 B1 * | 6/2016 | Whipple | A61B 17/7055 |
| 2001/0000186 A1 | 4/2001 | Bramlet | |
| 2002/0087161 A1 | 7/2002 | Randall et al. | |
| 2002/0198527 A1 * | 12/2002 | Muckter | A61B 17/8685 |
| | | | 606/316 |
| 2003/0078584 A1 * | 4/2003 | Tipirneni | A61B 17/68 |
| | | | 606/916 |
| 2003/0236555 A1 * | 12/2003 | Thornes | A61B 17/0401 |
| | | | 606/232 |
| 2004/0097941 A1 * | 5/2004 | Weiner | A61B 17/685 |
| | | | 606/312 |
| 2004/0167519 A1 * | 8/2004 | Weiner | A61B 17/8665 |
| | | | 606/60 |
| 2004/0172031 A1 * | 9/2004 | Rubecamp | A61B 17/8685 |
| | | | 606/309 |
| 2004/0260297 A1 | 12/2004 | Padget et al. | |
| 2005/0143735 A1 * | 6/2005 | Kyle | A61B 17/8685 |
| | | | 606/60 |
| 2005/0222575 A1 * | 10/2005 | Ciccone | A61B 17/1615 |
| | | | 606/104 |
| 2005/0234459 A1 * | 10/2005 | Falahee | A61B 17/1757 |
| | | | 606/323 |
| 2006/0161261 A1 * | 7/2006 | Brown | A61F 2/28 |
| | | | 623/22.22 |
| 2006/0264954 A1 * | 11/2006 | Sweeney, II | A61B 17/8685 |
| | | | 606/312 |
| 2007/0014649 A1 * | 1/2007 | James | A61B 17/863 |
| | | | 411/81 |
| 2007/0162026 A1 * | 7/2007 | Tipirneni | A61B 17/68 |
| | | | 606/916 |
| 2007/0213732 A1 * | 9/2007 | Khanna | A61B 17/8685 |
| | | | 606/86 A |
| 2007/0260248 A1 * | 11/2007 | Tipirneni | A61B 17/68 |
| | | | 606/65 |
| 2008/0140082 A1 * | 6/2008 | Erdem | A61B 17/8805 |
| | | | 606/92 |
| 2008/0147126 A1 * | 6/2008 | Tipirneni | A61B 17/8869 |
| | | | 606/300 |
| 2008/0147127 A1 * | 6/2008 | Tipirneni | A61B 17/742 |
| | | | 606/301 |
| 2008/0177306 A1 | 7/2008 | Lamborne et al. | |
| 2008/0243191 A1 * | 10/2008 | Tipirneni | A61B 17/742 |
| | | | 606/280 |
| 2009/0099610 A1 * | 4/2009 | Johnson | A61B 17/844 |
| | | | 606/86 R |
| 2009/0131936 A1 * | 5/2009 | Tipirneni | A61B 17/683 |
| | | | 606/64 |

(56) References Cited

U.S. PATENT DOCUMENTS

| | | | |
|---|---|---|---|
| 2009/0131991 A1* | 5/2009 | Tipirneni | A61B 17/683 606/301 |
| 2009/0198288 A1* | 8/2009 | Hoof | A61B 17/8615 606/301 |
| 2009/0228008 A1* | 9/2009 | Justin | A61B 5/107 606/62 |
| 2009/0228049 A1 | 9/2009 | Park | |
| 2009/0254129 A1* | 10/2009 | Tipirneni | A61B 17/742 606/309 |
| 2009/0259261 A1* | 10/2009 | Reiley | A61B 17/8897 606/329 |
| 2009/0306718 A1* | 12/2009 | Tipirneni | A61B 17/683 606/263 |
| 2009/0312798 A1* | 12/2009 | Varela | A61B 17/7064 606/247 |
| 2010/0036440 A1 | 2/2010 | Morris et al. | |
| 2010/0168802 A1* | 7/2010 | Pathak | A61B 17/60 606/305 |
| 2010/0198267 A1* | 8/2010 | Vaidya | A61B 17/68 606/286 |
| 2010/0204700 A1* | 8/2010 | Falahee | A61B 17/7064 606/80 |
| 2010/0217329 A1* | 8/2010 | Brown | A61B 17/742 606/301 |
| 2010/0312292 A1* | 12/2010 | Tipirneni | A61B 17/92 606/86 R |
| 2011/0034925 A1* | 2/2011 | Tipirneni | A61B 17/683 606/62 |
| 2011/0071576 A1* | 3/2011 | Hadi | A61B 17/683 606/301 |
| 2011/0071578 A1* | 3/2011 | Colesanti | A61B 17/064 606/305 |
| 2011/0087296 A1* | 4/2011 | Reiley | A61B 17/68 606/303 |
| 2011/0137356 A1* | 6/2011 | Kollmer | A61B 17/1767 606/324 |
| 2011/0184519 A1* | 7/2011 | Trieu | A61B 17/7076 623/17.11 |
| 2011/0238181 A1* | 9/2011 | Trieu | A61B 17/1735 623/17.11 |
| 2011/0264229 A1* | 10/2011 | Donner | A61F 2/30988 623/18.11 |
| 2011/0295252 A1* | 12/2011 | Tipirneni | A61B 17/685 606/62 |
| 2012/0203352 A1* | 8/2012 | Perez, III | A61F 2/3601 623/23.11 |
| 2012/0239095 A1* | 9/2012 | Barrall | A61B 17/1655 606/301 |
| 2012/0245704 A1* | 9/2012 | Childs | A61B 17/7064 623/23.52 |
| 2013/0018427 A1* | 1/2013 | Pham | A61B 17/7055 606/301 |
| 2013/0030456 A1* | 1/2013 | Assell | A61B 17/84 606/170 |
| 2013/0035727 A1* | 2/2013 | Datta | A61B 17/7055 606/279 |
| 2013/0079776 A1* | 3/2013 | Zwirkoski | A61B 17/68 606/62 |
| 2013/0158609 A1* | 6/2013 | Mikhail | A61B 17/683 606/305 |
| 2013/0190772 A1* | 7/2013 | Doerr | A61B 17/86 606/104 |
| 2013/0226239 A1* | 8/2013 | Altarac | A61B 17/7064 606/247 |
| 2013/0267836 A1* | 10/2013 | Mauldin | A61B 6/12 600/424 |
| 2013/0296953 A1* | 11/2013 | Mauldin | A61B 17/84 606/328 |
| 2014/0031935 A1* | 1/2014 | Donner | A61F 2/4455 623/17.11 |
| 2014/0046380 A1* | 2/2014 | Asfora | A61B 17/1615 606/304 |
| 2014/0135850 A1* | 5/2014 | Parent | A61B 17/68 606/304 |
| 2014/0135927 A1* | 5/2014 | Pavlov | A61B 17/7055 623/17.11 |
| 2014/0142700 A1* | 5/2014 | Donner | A61F 2/44 623/17.11 |
| 2014/0228898 A1* | 8/2014 | Gordon | A61B 17/84 606/328 |
| 2014/0236242 A1* | 8/2014 | Robinson | A61B 17/8605 606/279 |
| 2014/0257408 A1* | 9/2014 | Trieu | A61B 17/8875 606/301 |
| 2014/0257412 A1* | 9/2014 | Patty | A61B 17/8615 606/308 |
| 2014/0276827 A1* | 9/2014 | Roman | A61B 17/7291 606/64 |
| 2014/0276851 A1* | 9/2014 | Schneider | A61B 17/846 606/84 |
| 2014/0277139 A1* | 9/2014 | Vrionis | A61B 17/70 606/246 |
| 2014/0277460 A1* | 9/2014 | Schifano | A61F 2/4611 623/17.11 |
| 2014/0277463 A1* | 9/2014 | Yerby | A61F 2/32 623/17.11 |
| 2014/0277558 A1* | 9/2014 | Kurtz | A61B 17/0401 623/22.36 |
| 2014/0288601 A1* | 9/2014 | Baynham | A61B 17/7064 606/247 |
| 2014/0288605 A1* | 9/2014 | Mesiwala | A61B 17/7055 606/279 |
| 2015/0048057 A1* | 2/2015 | Wada | B23K 9/167 219/75 |
| 2015/0094765 A1* | 4/2015 | Donner | A61B 17/1735 606/246 |
| 2015/0105828 A1* | 4/2015 | Reckling | A61B 17/1659 606/279 |
| 2015/0150615 A1* | 6/2015 | Anapliotis | A61B 17/8685 606/305 |
| 2015/0157425 A1* | 6/2015 | Bar Shalom | A61C 8/0025 433/174 |
| 2015/0201985 A1* | 7/2015 | Rampersaud | A61B 17/8875 606/86 A |
| 2015/0216565 A1* | 8/2015 | Paley | A61B 17/68 606/328 |
| 2015/0257800 A1* | 9/2015 | Harshman | A61B 17/7208 606/62 |
| 2015/0320450 A1* | 11/2015 | Mootien | A61B 17/1703 606/246 |
| 2015/0320451 A1* | 11/2015 | Mootien | A61B 17/8685 606/246 |
| 2015/0320464 A1* | 11/2015 | Schmidt | A61B 17/863 606/304 |
| 2015/0342656 A1* | 12/2015 | Bertollo | A61B 17/8685 606/304 |
| 2015/0342753 A1* | 12/2015 | Donner | A61B 17/1757 623/18.11 |
| 2016/0015483 A1* | 1/2016 | Kumar | A61C 8/0012 606/301 |
| 2016/0030096 A1* | 2/2016 | Roman | A61F 2/4225 606/62 |
| 2016/0038186 A1* | 2/2016 | Herzog | A61B 17/683 606/304 |
| 2016/0040708 A1* | 2/2016 | Limatoc | F16B 39/284 411/306 |

(56) References Cited

U.S. PATENT DOCUMENTS

| | | | |
|---|---|---|---|
| 2016/0120661 A1* | 5/2016 | Schell | A61F 2/4601 623/17.11 |
| 2016/0143671 A1* | 5/2016 | Jimenez | A61B 17/7055 606/304 |
| 2016/0157897 A1* | 6/2016 | Vaidya | A61B 17/8066 606/279 |

FOREIGN PATENT DOCUMENTS

| | | |
|---|---|---|
| EP | 0085493 | 8/1983 |
| EP | 0260222 | 3/1988 |
| FR | 1046555 | 12/1953 |
| WO | WO 2010/019384 | 2/2010 |

OTHER PUBLICATIONS

Acharya NK, Bijukachhe B, Kumar RJ, Menon VK. Illio-lumbar fixation—the Amrita technique. J Spinal Disord Tech. Oct. 2008;21(7):493-9.

Ebraheim NA, Coombs R, Jackson WT, Rusin JJ. Percutaneous computed tomography-guided stabilization of posterior pelvic fractures. Clin Orthop Relat Res. Oct. 1994;(307):222-8.

Ebraheim NA, Padanilam TG, Waldrop JT, Yeasting RA. Anatomic consideration in the anterior approach to the sacro-iliac joint. Spine (Phila Pa 1976). Mar. 15, 1994;19(6):721-5.

Fuchs T, Rottbeck U, Hofbauer V, Raschke M, Stange R. [Pelvic ring fractures in the elderly. Underestimated osteoporotic fracture]. Unfallchirurg. Aug. 2011;114(8):663-70.

Gänsslen A, Krettek C. Retrograde transpubic screw fixation of transpubic instabilities. Oper Orthop Traumatol. Oct. 2006;18(4):330-40.

Gänsslen A, Hüfner T, Krettek C. Percutaneous iliosacral screw fixation of unstable pelvic injuries by conventional fluoroscopy. Oper Orthop Traumatol. Sep. 2006;18(3):225-44.

Gardner MJ, Routt ML Jr. Transiliac-transsacral screws for posterior pelvic stabilization. J Orthop Trauma. Jun. 2011;25(6):378-84.

Iguchi T, Ogawa K, Doi T, Miyasho K, Munetomo K, Hiraki T, Ozaki T, Kanazawa S. Computed tomography fluoroscopy-guided placement of iliosacral screws in patients with unstable posterior pelvic fractures. Skeletal Radiol. Jul. 2010;39(7):701-5.

Sciulli RL, Daffner RH, Altman DT, Altman GT, Sewecke JJ. CT-guided iliosacral screw placement: technique and clinical experience. AJR Am J Roentgenol. Feb. 2007;188(2).

Schildhauer TA, Ledoux WR, Chapman JR, Henley MB, Tencer AF, Routt ML Jr. Triangular osteosynthesis and iliosacral screw fixation for unstable sacral fractures: a cadaveric and biomechanical evaluation under cyclic loads. J Orthop Trauma. Jan. 2003;17(1):22-31.

Sciubba DM, Petteys RJ, Dekutoski MB, Fisher CG, Fehlings MG, Ondra SL, Rhines LD, Gokaslan ZL. Diagnosis and management of metastatic spine disease. A review. J Neurosurg Spine. Jul. 2010;13(1):94-108.

Pohlemann T, Gänsslen A, Tscherne H. [Fracture of the sacrum]. Unfallchirurg. Sep. 2000;103(9):769-86.

Pohlemann T, Richter M, Otte D, Gänsslen A, Bartram H, Tscherne H. [Mechanism of pelvic girdle injuries in street traffic. Medical-technical accident analysis]. Unfallchirurg. Apr. 2000;103(4):267-74.

Suzuki T, Hak DJ, Ziran BH, Adams SA, Stahel PF, Morgan SJ, Smith WR. Outcome and complications of posterior transiliac plating for vertically unstable sacral fractures. Injury. Apr. 2009;40(4):405-9.

Anselmetti GC, Bonaldi G, Carpeggiani P, Manfrè L, Masala S, Muto M. Vertebral augmentation: 7 years experience. Acta Neurochir Suppl. 2011;108:147-61. doi:10.1007/978-3-211-99370-5_23. Review. PubMed PMID: 21107952.

Butler CL, Given CA 2nd, Michel SJ, Tibbs PA. Percutaneous sacroplasty for the treatment of sacral insufficiency fractures. AJR Am J Roentgenol. Jun. 2005;184(6):1956-9. PubMed PMID: 15908561.

Frey ME, Depalma MJ, Cifu DX, Bhagia SM, Carne W, Daitch JS. Percutaneous sacroplasty for osteoporotic sacral insufficiency fractures: a prospective, multicenter, observational pilot study. Spine J. Mar.-Apr. 2008;8(2):367-73. Epub Jul. 20, 2007.

Garant M. Sacroplasty: a new treatment for sacral insufficiency fracture. J Vasc Interv Radiol. Dec. 2002;13(12):1265-7.

Heron J, Connell DA, James SL. CT-guided sacroplasty for the treatment of sacral insufficiency fractures. Clin Radiol. Nov. 2007;62(11):1094-100; discussion 1101-3. Epub Aug. 13, 2007.

Ortiz AO, Brook AL. Sacroplasty. Tech Vasc Interv Radiol. Mar. 2009;12(1):51-63.

Pommersheim W, Huang-Hellinger F, Baker M, Morris P. Sacroplasty: a treatment for sacral insufficiency fractures. AJNR Am J Neuroradiol. May 2003;24(5):1003-7.

Zaman FM, Frey M, Slipman CW. Sacral stress fractures. Curr Sports Med Rep. Feb. 5, 2006,(1):37-43.

Sagi HC. Technical aspects and recommended treatment algorithms in triangular osteosynthesis and spinopelvic fixation for vertical shear transforaminal sacral fractures. J Orthop Trauma. May-Jun. 2009;23(5):354-60.

Sagi HC, Militano U, Caron T, Lindvall E. A comprehensive analysis with minimum 1-year follow-up of vertically unstable transforaminal sacral fractures treated with triangular osteosynthesis. J Orthop Trauma. May-Jun. 2009;23(5):313-9; discussion 319-21.

\* cited by examiner

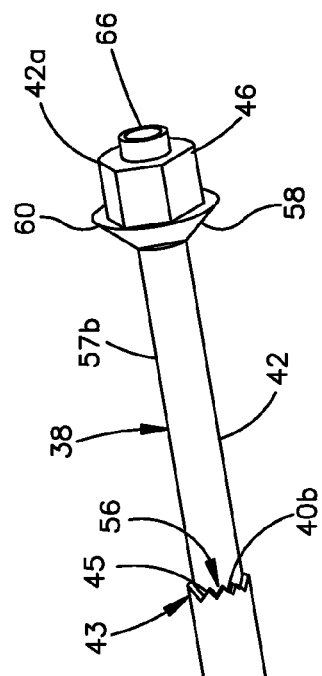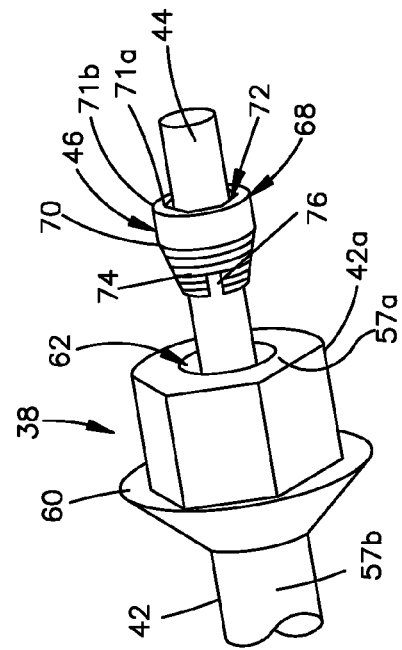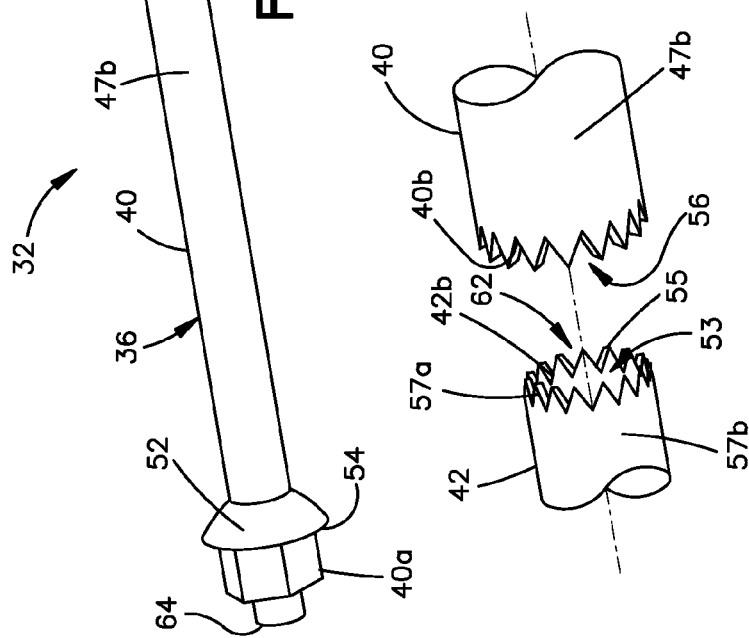

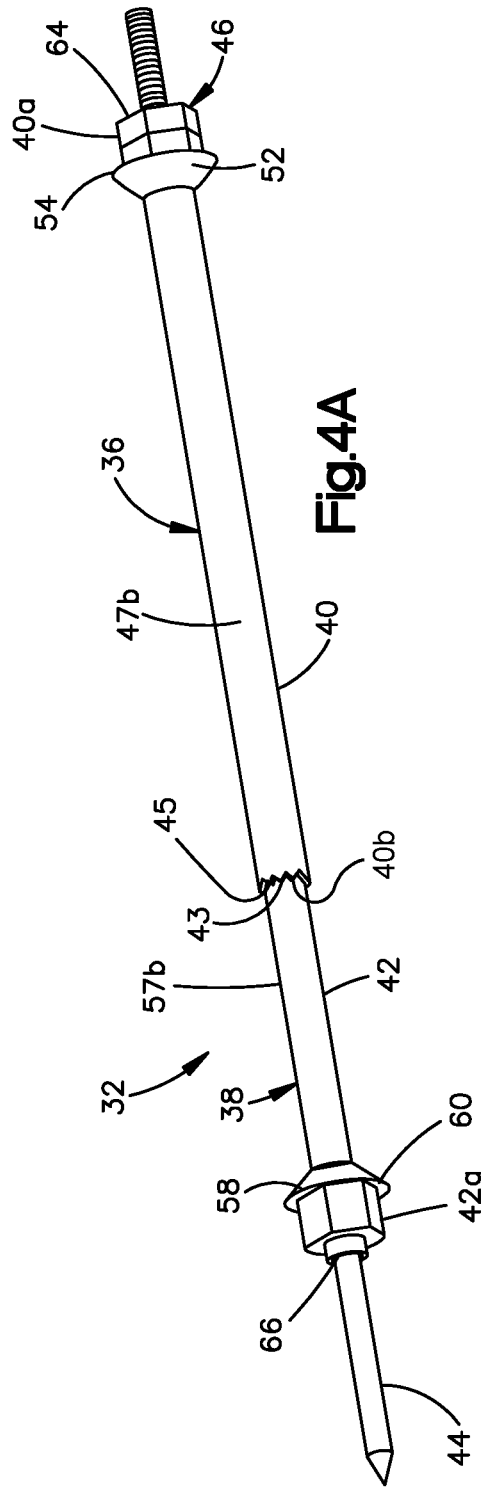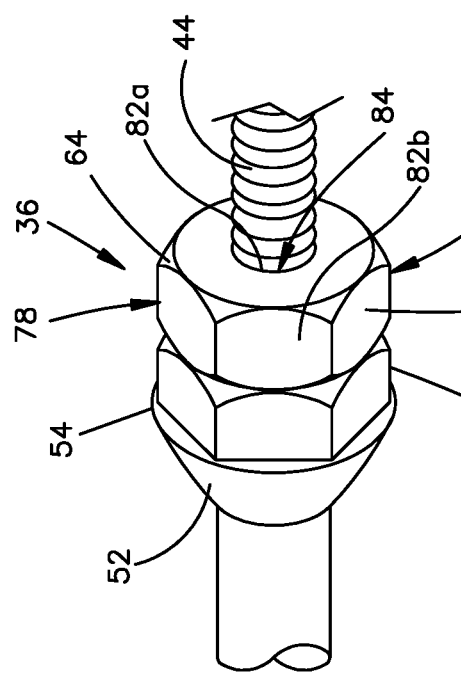

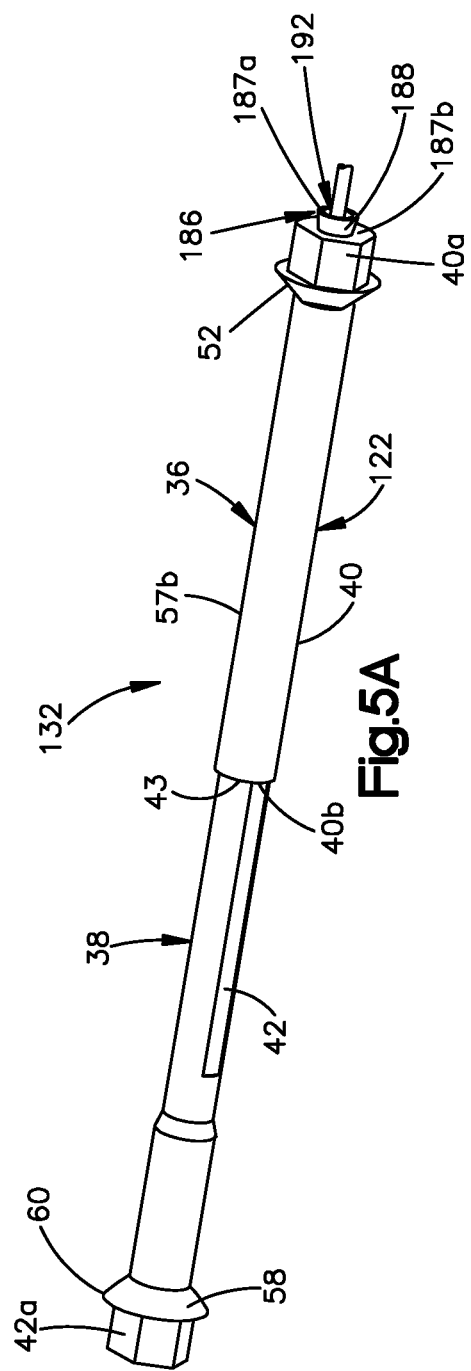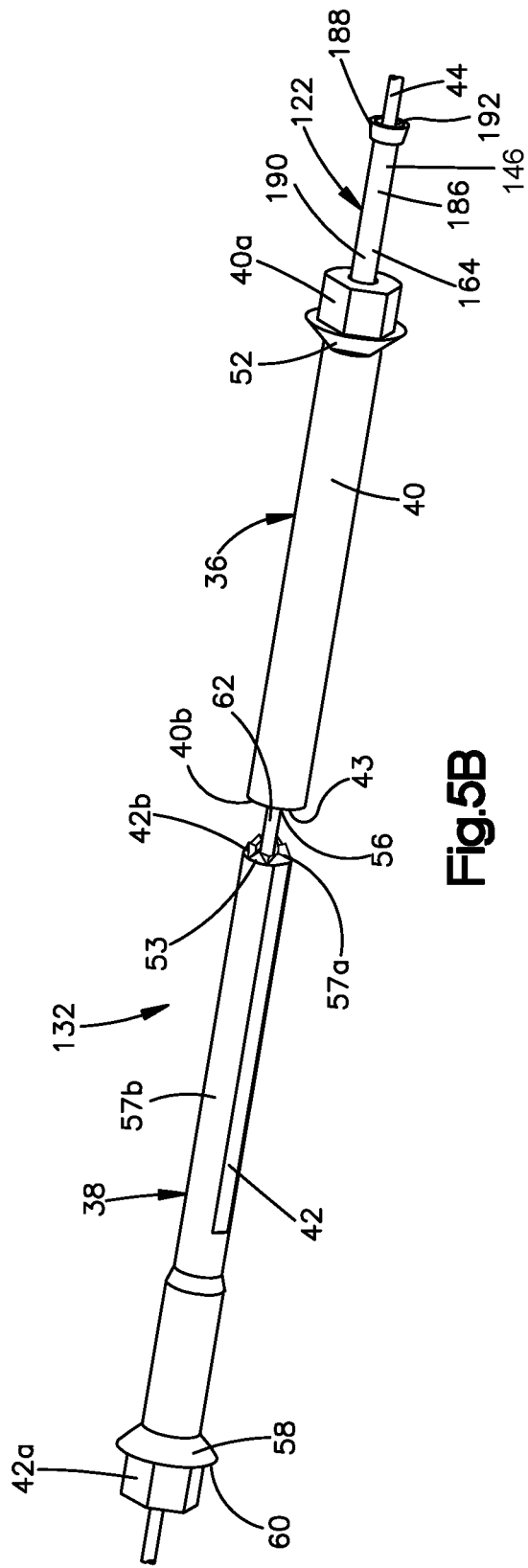

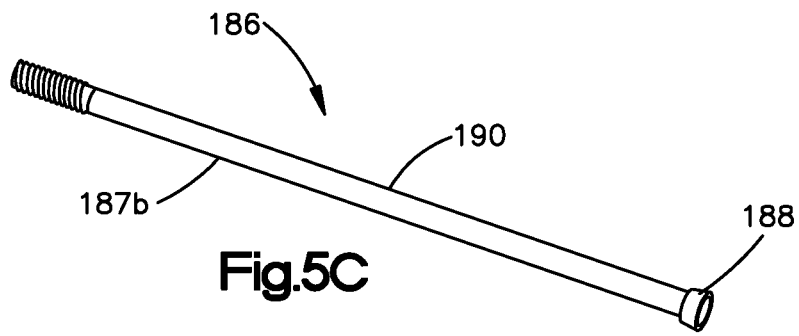
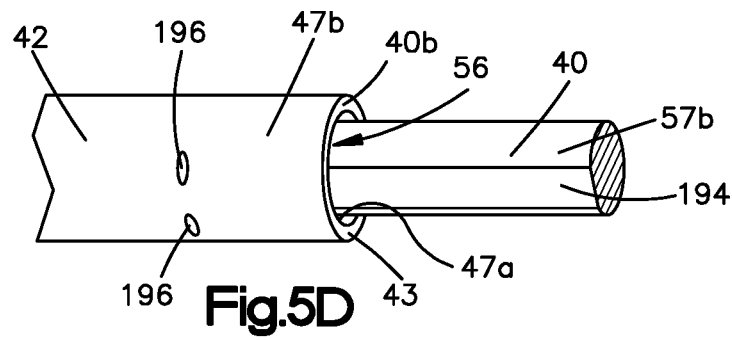
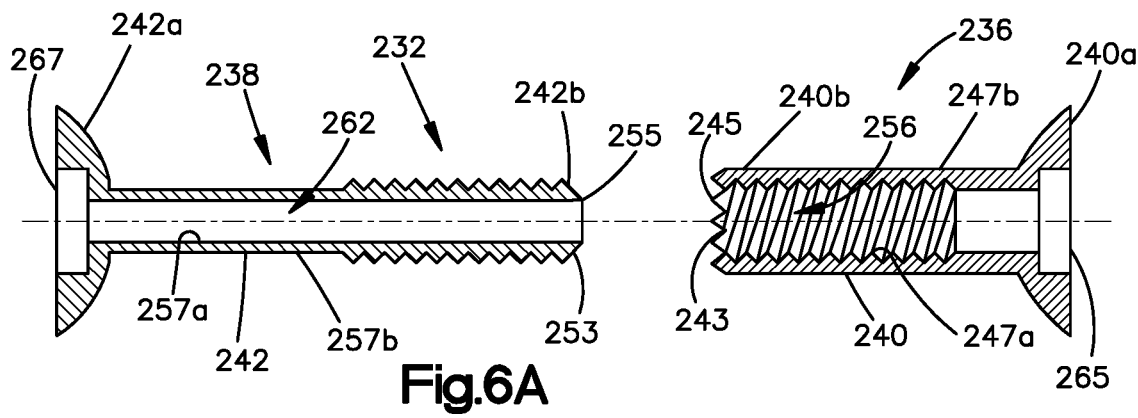
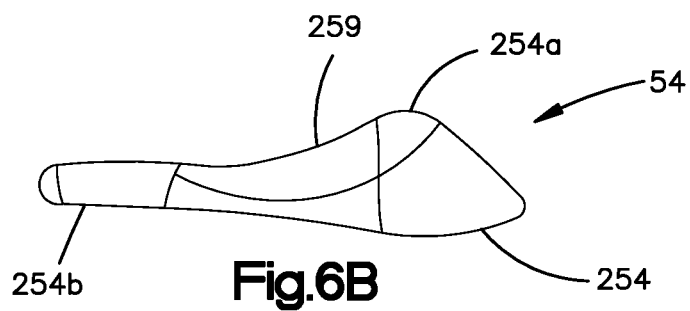

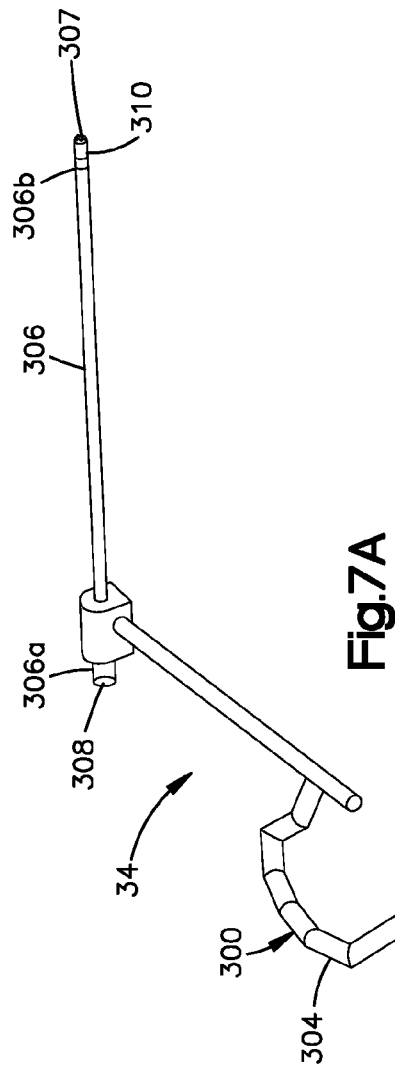
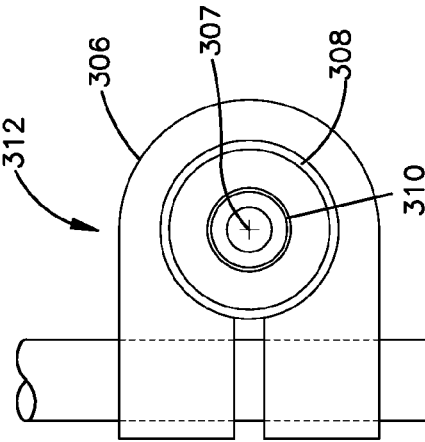
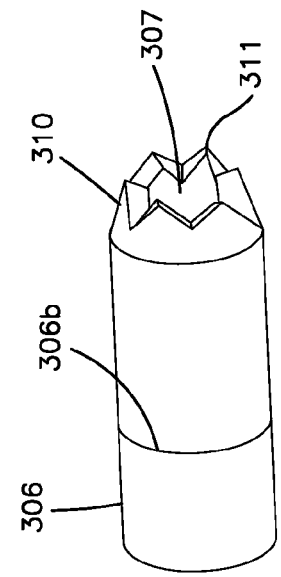

SACRAL FIXATION SYSTEM

CROSS-REFERENCE TO RELATED APPLICATIONS

This claims the benefit of U.S. Patent Application Ser. No. 61/991,829 filed May 12, 2014, and further claims the benefit of U.S. Patent Application Ser. No. 61/992,105 filed May 12, 2014, the disclosure of each of which is hereby incorporated by reference as if set forth in its entirety herein.

BACKGROUND

Implants for securing portions of a bone with respect to each other in order to promote bone healing are known. For instance, referring to FIG. 1, when a sacrum is fractured, conventional implant systems 20 such trans-iliac bars 22 are configured to support first and second ilium bones 24 and 26 with respect to each other, thereby stabilizing the sacral fracture. The trans-iliac bars 22 have a sufficient thickness to absorb the stresses experienced during use. While conventional trans-iliac bars 22 are suitable for their intended purpose, they have disadvantages because the surgeon cuts the ends after setting the bar into position. Due to the thickness of the trans-iliac bars 22, the surgical procedure typically involves a relatively large surgical field. Thus, the surgical procedure can be invasive, using a large incision in order to access and cut the trans-iliac bars with a suitably robust cutting instrument.

SUMMARY

In a first aspect of the present disclosure, a sacral fixation implant includes a first implant segment having a first shaft sized to be inserted through a first bone location, which can be defined by a first ilium bone. The first implant segment defines a first proximal end and a first distal end opposite the first proximal end. The first implant segment can define a first abutment surface that extends out from the first shaft and is configured to abut the first bone location so as to prevent further insertion through the first bone location. The first implant segment can further define a first channel that extends through the first shaft from the first proximal end to the first distal end. The sacral fixation system can further include a second implant segment having a second shaft sized to be inserted through a second bone location, which can be defined by a second iliac bone. The second implant segment defines a second proximal end and a second distal end opposite the second proximal end. The second implant segment can define a second abutment surface that extends out from the second shaft and is configured to abut the second bone location so as to prevent further insertion through the second bone location. At least the second distal end can be sized to be received in the first channel at a location between the first and second bone locations. The sacral fixation system can further include at least one locking member that is configured to fix the first and second implant segments with respect to movement of the first and second implant segments away from each other, wherein the at least one locking member is separate from each of the first and second implant segments, and does not extend through the first and second shafts from the first proximal end to the second proximal end.

BRIEF DESCRIPTION OF THE DRAWINGS

The foregoing summary, as well as the following detailed description of embodiments of the application, will be better understood when read in conjunction with the appended drawings. For the purposes of illustrating the methods, implants and systems of the present application, there is shown in the drawings preferred embodiments. It should be understood, however, that the application is not limited to the precise methods, implants, and systems shown. In the drawings:

FIG. 3A is a perspective view of a portion of a sacral fixation implant configured to be included in the sacral implant system illustrated in FIG. 2, the implant including first and second implant segments, and first and second locking members configured to secure the first and second implant segments to a guide wire;

FIG. 3B is a perspective view of distal ends of first and second implant segments of the implant illustrated in FIG. 3A;

FIG. 3C is a perspective view of a portion of the first implant segment illustrated in FIG. 3A, showing attachment of the first locking member;

FIG. 4A is a perspective view of a portion of a sacral fixation implant similar to the sacral fixation implant as illustrated in FIG. 3A, but including a locking member constructed in accordance with an alternative embodiment;

FIG. 4B is a perspective view of a portion of the first implant segment illustrated in FIG. 4A, but showing attachment of the locking member constructed in accordance with the alternative embodiment;

FIG. 5A is a perspective view of a portion of another sacral fixation implant configured to be included in the sacral fixation implant illustrated in FIG. 2, the sacral fixation implant including first and second implant segments and a fixation member configured to secure the first and second implant segments to each other;

FIG. 5B is an exploded perspective view of the sacral fixation implant illustrated in FIG. 5A;

FIG. 5C is a perspective view of the fixation member illustrated in FIG. 5A;

FIG. 5D is a perspective view of a region of the sacral fixation implant illustrated in FIG. 5A, whereby the first implant segment receives the second implant segment;

FIG. 6A is a perspective view of a sacral fixation implant configured to be included in the sacral fixation system illustrated in FIG. 2, the sacral fixation implant constructed in accordance with another alternative embodiment;

FIG. 6B is a side elevation view of an abutment member of the sacral fixation implant illustrated in FIG. 6A;

FIG. 7A is a perspective view of a targeting device constructed in accordance with one embodiment;

FIG. 7B is an enlarged perspective view of a cutting tip of the targeting device illustrated in FIG. 7A; and FIG. 7C is an end elevation view showing the targeting device aligned with an imaging source.

DETAILED DESCRIPTION

Figure 1:
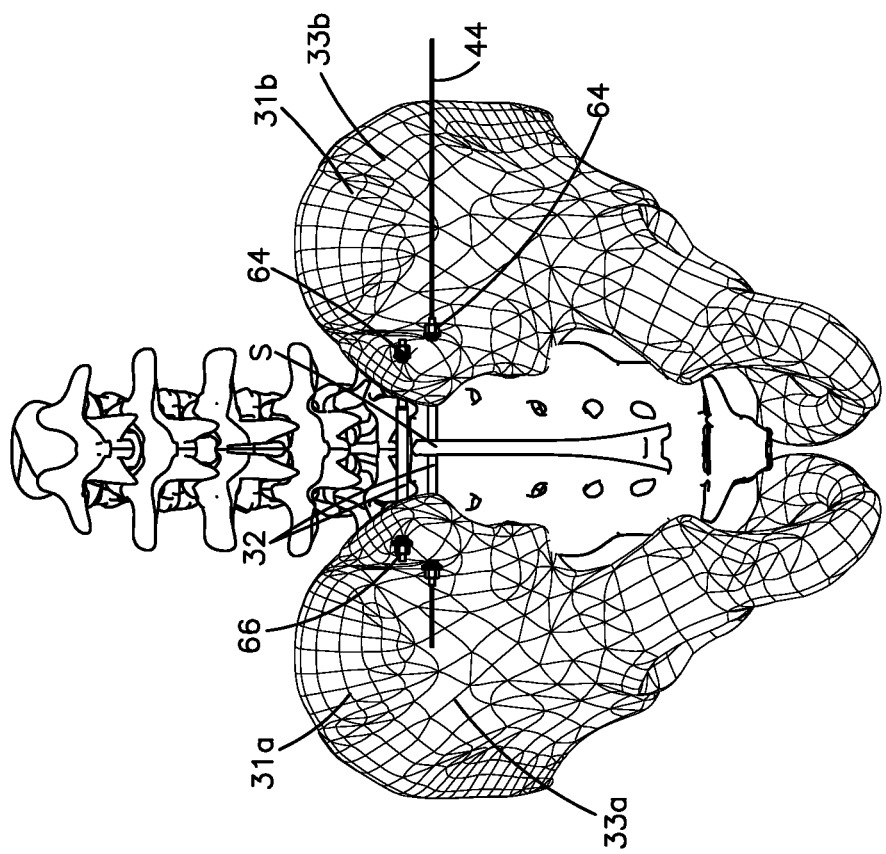
FIG. 1 is a posterior view of a human sacral region and a conventional sacral implant system fixed to the sacral region.

Referring to FIGS. 2 to 7C generally, a sacral fixation system 30 constructed in accordance with one embodiment includes one or more bone fixation implants configured to be implanted into first and second bone locations 31a and 31b of a patient's body. In accordance with certain embodiments, the sacral fixation system 30 can further include a targeting device 34 configured to align a corresponding guide wire for insertion into or through the respective first and second bone locations of the bone fixation implants. Each of the bone fixation implants 32 can include a first implant segment 36, which can include a first shaft 40. Each of the bone fixation implants 32 can further include a second implant segment 38, which can include a second shaft 42. In accordance with certain embodiments, the sacral fixation system can include a guide wire 44. The guide wire 44 is configured to be received by each of the first and second implant segments 36 and 38 so as to guide each of the first and second implant segments 36 and 38 to the respective first and second bone locations 31a and 31b. In accordance with certain examples, the guide wire 44 is further configured to be secured to each of the first and second implant segments 36 and 38 so as to prevent movement of the first and second implants 36 and 38 away from each other. In other examples, the guide wire 44 is further configured to be secured to each of the first and second implant segments 36 and 38 so as to prevent movement of the first and second implants 36 and 38 toward from each other. The guide wire 44 can be configured as a Kirschner wire, or any suitable alternative guide wire as desired.

In use, the guide wire 44 can be driven through the first and second bone locations 31a and 31b. The first implant segment 36 is inserted over the guide wire 44 and driven through the first bone location 31a. In certain examples, the first implant segment 36 is configured to drill a bore hole through the first bone location 31a. Alternatively, the bore hole can be pre-drilled. The second implant segment 38 is inserted over the guide wire 44 and driven through the second bone location 31b. In certain examples, the second implant segment 36 is configured to drill a bore hole through the second bone location 31b. Alternatively, the bore hole can be pre-drilled. The second implant segment 38 is driven through the second bone location 31b until a distal end of the second implant segment 38 is received by the first implant segment 36. The bone fixation implant 32 further includes a fixation mechanism 46 configured to fix the first and second implant segments 36 and 38 with respect to translation of the first and second implant segments 36 and 38 away from each other.

The first bone location 31a, for instance, can be defined by a first ilium bone 33a, and the second bone location 31b can be defined by a second ilium bone 33b that is separated from the first ilium bone 33a by a sacrum S, and thus disposed on opposite sides of the sacrum S. Thus, each of the bone fixation implants 32 can be referred to as a sacral fixation implant. For instance, the first ilium bone 33a can be defined by the left hip, and the second ilium bone 33b can be defined by the right hip. Alternatively, the first bone location 31a can be defined by the second ilium bone 33b, and the second bone location 31b can be defined by the first ilium bone 33a. It will be appreciated that the bone fixation implants 32 are configured to be implanted in accordance with minimally-invasive surgical (MIS) techniques, where small incisions are sufficient to facilitate implantation and fixation of the implant segments to the first and second bone locations. The sacral fixation system 20 and its components can be manufactured from any suitable material, for example, metals such as titanium or steel or polymers such as Polyetheretherkeytone (PEEK) or reinforced PEEK. In one embodiment, the sacral fixation system 30 can include at least one implant 32 that extends through the first and second ilium bones 33a and 33b without passing through the sacrum S. Alternatively or additionally, the sacral fixation system 30 can include at least one implant that extends through both the first and second ilium bones 33a and 33b, and further extends through the sacrum S.

Referring now to FIGS. 2-4B, the first implant segment 36 can include the first shaft 40 that is sized to be inserted through the first bone location 31a. The first shaft 40, and thus the first implant segment 36, can define a first proximal end 40a and a first distal end 40b opposite the first proximal end 40a. When the implant segment 36 is implanted in the first bone location 31a, the first proximal end 40a can define a lateral end, and the first distal end 40b can define a medial end. The first shaft 40 can be elongate along a first central axis between the first proximal end 40a and the first distal end 40b. At least a portion up to an entirety of the first central axis can be linear. The first shaft 40 can be cylindrical in shape, or can define any suitable alternative shape as desired.

The first implant segment 36 can include a first abutment surface 52 that extends out from the first shaft 40. For instance, the first abutment surface 52 can be disposed proximate to the first proximal end 40a. In one example, the first implant segment 36 can include a first abutment member 54 that extends out from the first shaft 40. The first abutment member 54 can be raised with respect to the first shaft 40 away from the first central axis, such that the first abutment member 54 defines the first abutment surface 52. In this regard, it should be appreciated that the first abutment member 54 can be monolithic with the first shaft 40. Alternatively, the first abutment member 54, and the corresponding first abutment surface 52, can be separate from the first shaft 40 and attached to the first shaft 40. For instance, the first abutment member 54 can be in the form of a washer, clip, or other like structure that is configured to be supported by the first shaft 40 so as to define the first abutment surface. For instance, the washer can be configured as a washer 254 described in more detail below with respect to FIG. 6.

The first implant segment 36 can define a substantially constant first outer cross-sectional dimension from the distal end 40b to the first abutment surface 52. The first outer cross-sectional dimension extends through the first central axis, and can be a diameter or any suitable alternative cross-sectional dimension as desired. The first implant segment 36 can be annular. For instance, the first implant segment 36 can further define a first channel 56 that extends through the first shaft 40 from the first proximal end 40a to the first distal end 40b. The first channel 56 can extend along the first central axis. Thus, the first shaft 40 can define an inner surface 47a that defines the first channel 56, and an outer surface 47b opposite the inner surface 47a. The first channel 56 is sized to receive the guide wire 44.

In one example, referring to FIG. 3B, the first distal end 40b can define an annular tip 43 that can be serrated, such that the serrations extend out in the first direction from the first proximal end 40a toward the first distal end 40b. The annular tip defines a cutting surface 45 that is configured to drill a hole into the first bone location 31a. For instance, the cutting surface 45 can be placed against the first bone location 31a and the first shaft 40 can be rotated about the first central axis so that the serrated cutting surface 45 creates a bore hole in the first bone location 31a. Thus, the first shaft 40 can be referred to as self-drilling. As described above with respect to FIG. 2, the bone fixation implant 32 can be configured to extend through the sacrum S if desired. Accordingly, it should be appreciated, for instance when the implant 32 is to extend through the sacrum S, the cutting surface 45 can create bore hole in the sacrum after being driven through the first bone location 31a. Alternatively, a cutting instrument can create the bore hole in the first bone location 31a prior to insertion of the first shaft 40 through the first bone location 31a, as will be described in more detail below. The cutting instrument can further create the bore hole in the sacrum S if desired. Thus, it should be appreciated that the annular tip can alternatively define a smooth surface as desired.

Referring again to FIGS. 2-4B, the second implant segment 38 can include the second shaft 42 that is sized to be inserted through the second bone location 31b. The second shaft 42, and thus the second implant segment 38, can define a second proximal end 42a and a second distal end 42b opposite the second proximal end 42a. When the second implant segment 38 is implanted in the second bone location 31b, the second proximal end 42a can define a lateral end, and the second distal end 42b can define a medial end. The second shaft 42 can be elongate along a second central axis between the second proximal end 42a and the second distal end 42b. At least a portion up to an entirety of the second central axis can be linear. The second shaft 42 can be cylindrical in shape, or can define any suitable alternative shape as desired. At least a portion of the second shaft 42 can be sized to be received in the first channel 56. For instance, at least the second distal end 42b can define a cross-sectional dimension that is slightly less than that of the first channel 56. When the second shaft 42 is received in the first channel 56, the first and second central axes can be coincident with each other.

The second implant segment 38 can include a second abutment surface 58 that extends out from the second shaft 42. For instance, the second abutment surface 58 can be disposed proximate to the second proximal end 42a. In one example, the second implant segment 38 can include a second abutment member 60 that extends out from the second shaft 42. The second abutment member 60 can be raised with respect to the second shaft 42 away from the second central axis, such that the second abutment member 60 defines the second abutment surface 58. In this regard, it should be appreciated that the second abutment member 60 can be monolithic with the second shaft 42. Alternatively, the second abutment member 60, and the corresponding second abutment surface 58, can be separate from the second shaft 42 and attached to the second shaft 42. For instance, the second abutment member 60 can be in the form of a washer, clip, or other like structure that is configured to be supported by the second shaft 42 so as to define the second abutment surface. For instance, the washer can be configured as a washer 254 described in more detail below with respect to FIG. 6. The second implant segment 38 can define a substantially constant second outer cross-sectional dimension from the second distal end 42b to the second abutment surface 58. The second outer cross-sectional dimension extends through the second central axis, and can be a diameter or any suitable alternative cross-sectional dimension as desired.

The second implant segment 38 can be annular. For instance, the second implant segment 38 can further define a second channel 62 that extends through the second shaft 42 from the second proximal end 42a to the second distal end 42b. Thus, the second shaft 42 can define an inner surface 57a that defines the second channel 62, and an outer surface 57b opposite the inner surface 57a. The second channel 62 can extend along the second central axis, and can have a cross-sectional dimension slightly greater than that of the guide wire 44, such that the second channel 62 is sized to receive the guide wire 44. Accordingly, the cross-sectional dimension of the second channel 62 is less than the cross-sectional dimension of at least a portion of the first channel 56 that receives the second shaft 42. The first and second cross-sectional dimensions can extend through the first and second central axes, respectively, and can define diameters or any suitable cross-sectional dimensions as desired.

In one example, as illustrated in FIG. 3B, the second distal end 42b can define a second annular tip 53 that can be serrated, such that the serrations extend out in the second direction from the second proximal end 42a toward the second distal end 42b. Accordingly, the second annular tip 53 defines a second cutting surface 55 that is configured to drill a hole into the second bone location 31b. For instance, the second cutting surface 55 can be placed against the second bone location 31b and the second shaft 42 can be rotated about the second central axis so that the serrated cutting surface 55 creates a bore hole in the second bone location 31b. Thus, the second shaft 42 can be referred to as self-drilling. As described above with respect to FIG. 2, the bone fixation implant 32 can be configured to extend through the sacrum S if desired. Accordingly, it should be appreciated, for instance when the implant 32 is to extend through the sacrum S, the second cutting surface 55 can create bore hole in the sacrum after being driven through the second bone location 31b. Alternatively, a cutting instrument can create the bore hole in the second bone location 31b prior to insertion of the second shaft 42 through the second bone location 31b, as will be described in more detail below. Thus, it should be appreciated that the second annular tip 53 can alternatively define a smooth surface as desired.

Referring now to FIGS. 2-4B, during operation, the guide wire 44 is placed across the sacroiliac joint from the first bone location 31a, such as the first ilium bone 33a, to the second bone location 31b, such as the second ilium bone 33b. Next, the first channel 56 receives the guide wire 44, and the first distal end 40b of the first shaft 40 is configured to be inserted through one of the first and second ilium bones 33a and 33b along the guide wire 44. For instance, the first shaft 40 can be inserted through the first bone location 31a in a first direction toward the second bone location 31b until the first abutment surface 52 abuts the first bone location 31a. The first channel 56 receives the guide wire 44, and advances along the guide wire 44, as the first shaft 40 is inserted through the first bone location 31a. Thus, the first abutment surface 52 is configured to abut the first bone location 31a so as to prevent further insertion of the first shaft 40 through the first bone location 31a.

The second distal end 42b of the second shaft 42 is configured to be inserted through the other of the first and second bone locations 31a and 31b. For instance, the second shaft 42 can be inserted through the second bone location 31b in a second direction, opposite the first direction, toward the first bone location 31a such that at least the second distal end 42b is received in the first channel 56 at a location between the first and second bone locations 31a and 31b. The second shaft 42 is inserted in the second direction, and the second distal end 42b is advanced in the first channel 56 toward the first proximal end 40a, until the second abutment surface 58 abuts the second bone location 31b. The second channel 62 receives the guide wire 44, and advances along the guide wire 44, as the second shaft 42 is inserted through the second bone location 31b, for instance, the second ilium bone 33b. Thus, the second abutment surface 58 is configured to abut the second bone location 31b so as to prevent further insertion of the second shaft 42 through the second bone location 31b. It should be appreciated that the first shaft 40 can be advanced through the first bone location 31a before, after, or simultaneously with, insertion of the second shaft 42 through the second bone location 31b, such that the second shaft is received by the first channel 56. Subsequent further insertion of the first shaft 40, the second shaft 42, or both, through the respective first and second bone locations 31a and 31b further advances the second distal end 42b in the first channel 56 in the second direction. As described above, the first and second shafts 40 and 42 can extend through the first ilium bone 33a and the second ilium bone 33b, respectively, without passing through the sacrum S. Alternatively, one or both of the first and second shafts can further extend through the sacrum S.

With continuing reference to FIGS. 2-4B, and as described above, the fixation mechanism 46 is configured to fix the first and second implant segments 36 and 38 with respect to translation of the first and second implant segments 36 and 38 away from each other. It should be appreciated that mechanical interference between the first abutment surface 52 and the first bone location 31a fix the first implant segment 36 with respect to translation toward the second implant segment 38. Further, mechanical interference between the second abutment surface 58 and the second bone location 31b fixes the second implant segment 38 with respect to translation toward the first implant segment 36.

As will be appreciated from the description below, the fixation mechanism 46 is configured to secure the first implant segment to the second implant segment 38 via a threaded engagement. In one example, the fixation mechanism can include the guide wire 44 and at least one locking member that is configured to prevent at least one of the first and second shafts 40 and 42 from moving away from the other of the first and second shafts 40 and 42. Thus, the at least one locking member can prevent movement of the at least one or both of the first and second shafts 40 and 42 along the guide wire 44 in a direction from the respective distal end toward the respective proximal end. In certain examples, the at least one locking member can prevent movement of the at least one or both of the first and second shafts 40 and 42 along the guide wire in a direction from the respective proximal end toward the respective distal end. Further, it will be appreciated in certain examples that the at least one locking member does not extend through the implant from the first proximal end 40a to the second proximal end 42a. For instance, the fixation mechanism 46 can include first and second locking members 64 and 66. The first locking member 64 is configured to fix the first implant segment 36 to the guide wire 44 with respect to translation of the first implant segment 36 along the guide wire 44 in at least one direction, for instance in first and second opposed directions. The second locking member 66 is configured to fix the second implant segment 38 to the guide wire 44 with respect to translation of the second implant segment 38 along the guide wire 44 in at least one direction, for instance in first and second opposed directions. Thus, it should be appreciated that the guide wire 44 can be designed to remain permanently implanted in the sacral region. That is, the guide wire 44 remains implanted with the first and second implant segments 36 and 38 after completion of the surgical procedure. Otherwise stated, the guide wire 44 can remain implanted as long as the first implant 32 remains implanted.

As illustrated in FIG. 3C, either or both of the first and second locking members 64 and 66 can be configured as a locking cap 68. The locking cap 68 includes a locking cap body 70 and a channel 72 that extends through the locking cap body 70. The channel 72 is sized to receive the guide wire 44. For instance, the locking cap body 70 includes an inner surface 71a that defines the channel 72, and an outer surface 71b opposite the inner surface 71a. The locking cap body 70 further defines at least one flexible wall 74 wall that defines a portion of the channel 72. For instance, the inner surface 71a at the flexible wall 74 defines the channel 72 having an initial cross-sectional dimension that is greater than that of the guide wire 44. The outer surface 71b at the flexible wall 74 can be threaded, and can further be tapered as it extends in a distal direction. The flexible wall 74 is configured to compress against the guide wire 44 in response to a radially compression force applied to the flexible wall 74. In one example, the locking cap 68 can further define at least one compression slot 76 that extends radially through the flexible wall 74 so as to be open to the channel 72.

Referring to FIG. 3C, the locking cap 68 will be described in connection with the second proximal end 42a of the second shaft 42. It will be appreciated, of course, that when the first locking member 64 is configured as a locking cap 68, the locking cap 68 can similarly cooperate with the first proximal end 40a of the first shaft 40 as described herein with respect to the second proximal end 42a of the second shaft 42. The locking cap 68, and in particular the flexible wall 74, can receive the guide wire 44, such that the guide wire 44 extends through the channel 72. The locking cap 68 can be translated along the guide wire 44 in the distal direction toward the second proximal end 42a. The flexible wall 74 is sized to be at least partially received in an aperture that extends through the second proximal end 42a in the second direction. The aperture can, for instance, be defined by the second channel 62 that extends through the second shaft 42 from the proximal end 42a to the distal end 42b. The first shaft 40 likewise includes an aperture that that extends through the first proximal end 40a along the first direction. The aperture can, for instance, be defined by the first channel 56 that extends through the first shaft 40 from the first proximal end 40a to the first distal end 40b. Accordingly, the inner surface 57a that defines the second channel 62 can further define the aperture. The inner surface 57a at the aperture is configured to apply the compression force to the flexible wall 74 as the locking cap is inserted into the aperture. The compression force applied by the inner surface 57a thus causes the flexible wall 74 to compress against the guide wire 44 and attach the locking cap 68 to the guide wire.

It is appreciated that the flexible wall 74 can be externally threaded, and the inner surface 57a can likewise be threaded. Accordingly, once that locking cap 68 has been translated along the guide wire 44 to a location whereby the flexible wall 74 contacts the second shaft 42, the locking cap 68 can be rotated relative to the second shaft 42 about the guide wire 44 so as to threadedly mate the cap 68 to the second shaft 42. Because the flexible wall 74 is tapered in the second direction, as the locking cap 68 is advanced in the aperture of the proximal end 42a, the inner surface 57a compresses the flexible wall 74 against the guide wire 44 as described above. It should be appreciated that, alternative or additionally, the inner surface 57a can be tapered in the second direction. Because the locking cap 68 threadedly mates with the respective shaft 40 or 42, when both of the first and second locking members 64 and 66 are configured as locking caps 68, the locking caps 68 fix the first and second shafts 40 and 42 to the guide wire 44 without applying a compressive force to the shafts 40 and 42 that would compress the first and second ilium bones 33a and 33b toward each other. Thus, when the sacrum S (see FIG. 2) is fractured, the fracture can be reduced with, for example, reduction forceps or any suitable alternative structure, and the threaded locking caps 68 can secure the first and second shafts 40 and 42 to the guide wire 44 so as to maintain the fracture in its reduced configuration, thereby promoting bone healing. Further, it should be appreciated that the locking cap 68 can be configured to prevent movement of the second implant segment 38 along the guide wire 44 both in a direction from the second distal end 42*b* toward the second proximal end 42*a*, and in a direction from the second proximal end 42*a* toward the second distal end 42*b*.

Because the first locking member 64, and in particular the locking cap 68, can be configured to threadedly attach to the first implant segment 36 so as to fix the first implant segment 36 to the guide wire 44 which, in turn, is fixed to the second implant segment 38, the fixation mechanism 46 can be said to fix the first implant segment 36 to the second implant segment 38 via a threaded engagement. Further, because the second locking member 66, and in particular the locking cap 68, can be configured to threadedly attach to the second implant segment 38 so as to fix the second implant segment 38 to the guide wire 44 which, in turn, is fixed to the first implant segment 36, the fixation mechanism 46 can be said to fix the implant segment 36 to the second implant segment 38 via a threaded engagement.

Figure 2:
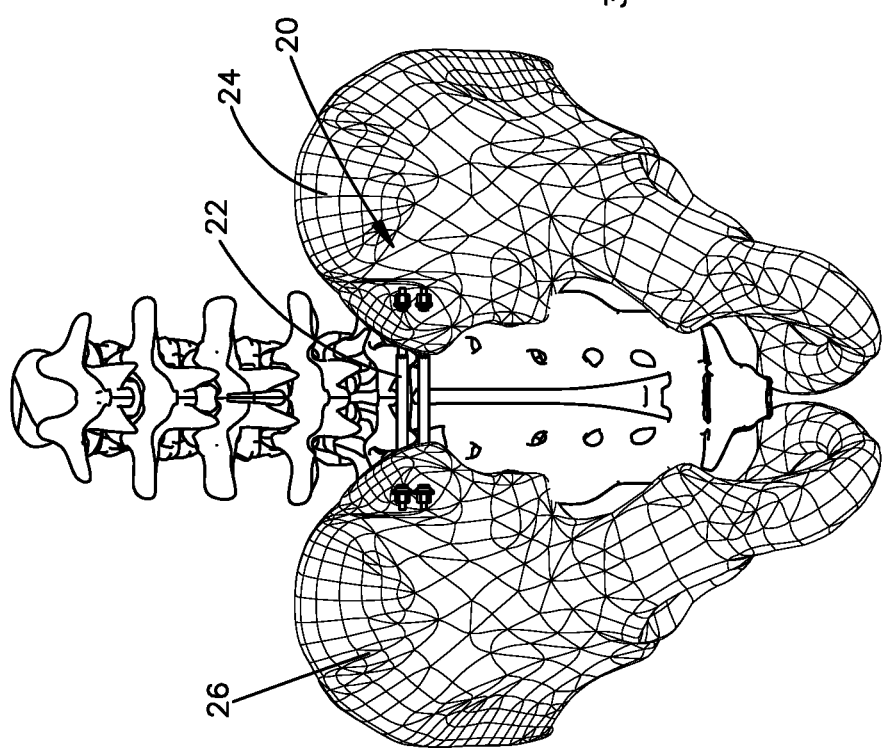
FIG. 2 is an anterior view of a human sacrum, showing a sacral implant system constructed in accordance with one embodiment of the present disclosure secured to first and second ilium bones.

Referring now also to FIGS. 2 and 4A-4B, it should be appreciated that at least one of the first and second locking members 64 and 66 can be configured as a locking nut 78. For instance, the first locking member 64 can be configured as a locking cap 68, and the second locking member 66 can be configured as a locking nut 78. Alternatively, the first locking member 64 can be configured as a locking nut 78, and the second locking member 66 can be configured as a locking cap 68. Alternatively still, each of the first and second locking members 64 and 66 can be configured as a respective locking nut 78. Alternatively still, each of the first and second locking members 64 and 66 can be configured as a respective locking cap 68.

The locking nut 78 will be described in connection with the first proximal end 40*a* of the first shaft 40. It will be appreciated, of course, that when the second locking member 66 is configured as a locking nut 78, the locking nut 78 can similarly cooperate with the second proximal end 42*a* of the second shaft 42 as described herein with respect to the first proximal end 40*a* of the first shaft 40. The locking nut 78 can define a nut body 80 having an inner surface 82*a* that defines a channel 84 that extends through the nut body 80, and an outer surface 82*b* opposite the inner surface 82*a*. The channel 84 is sized to receive the guide wire 44. The inner surface 82 can be threaded. Thus, the locking nut 78 can be said to be internally threaded. Further, at least a portion of the guide wire 44 can be externally threaded. The portion of the guide wire 44 can be disposed proximate to the first proximal end 40*a*, and can for instance extend from a first location spaced from the proximal end 40*a* in the second direction region to a second location spaced from the proximal end 40*a* in the first direction when the first abutment surface 52 is positioned adjacent the first bone location 31*a*.

As a result, the locking nut 78 is configured to be threaded onto the guide wire 44 and threadedly advanced along the guide wire 44 toward the first shaft 40 until the locking nut 78 abuts the first shaft 40. For instance, the locking nut 78 can abut the first proximal end 40*a*. Subsequent rotation of the locking nut 78 about the guide wire 44 while the second abutment surface 58 is in contact with the second bone location 31*b* therefore urges the first shaft 40 in the first direction toward the second shaft 42. Thus, when the first abutment surface 52 is in contact with the first bone location 31*a*, the compression nut is configured to apply a compressive force that is delivered to the first and second ilium bones 33*a* and 33*b* (see FIG. 2). In particular, the first shaft 40 extends through the first ilium bone 33*a* such that the first abutment surface 52 is in contact with the first ilium bone 33*a*, and the second shaft 42 extends through the is second ilium bone 33*b* and into the first shaft 40 until the second abutment surface 58 is in contact with the second ilium bone 33*b*. One of the first and second shafts 40 and 42 can be secured to the guide wire with respect to movement away from the other of the first and second shafts 40 and 42 in any manner described herein. The locking nut 78 is then advanced along the guide wire until it applies a compressive force to the other of the first and second shafts 40 and 42, thereby applying compression to each of the first and second ilium bones 33*a* and 33*b* toward the other of the first and second ilium bones 33*a* and 33*b*. When the sacrum S is fractured, the compression is used to promote bone healing. Since the implant 32 has the ability to maintain the compressive force throughout bone healing, the reduction of the fracture is maintained and bone healing promoted. As illustrated in FIG. 2, the sacral fixation system 30 can include first and second implants 32 which can each be constructed in accordance with any embodiment as described herein, and can be positioned at different locations at the ilium bones stabilize each of the ilium bones to each other, and in some examples to apply a compressive force to the sacrum S. It should be further appreciated that the fixation mechanism 46 can include at least one locking member that does not extend through the first and second shafts from the first proximal end to the second proximal end. For instance, the at least one locking member can be defined by one or both of the locking cap 68 and the locking nut 78.

Because the first locking member 64, an in particular the locking nut 78, can be configured to threadedly attach to the guide wire 44 so as to fix the first implant segment 36 to the guide wire 44 which, in turn, is fixed to the second implant segment 38, the fixation mechanism 46 can be said to fix the first implant segment 36 to the second implant segment 38 via a threaded engagement. Further, because the second locking member 66, an in particular the locking nut 78, can be configured to threadedly attach to the guide wire 44 so as to fix the second implant segment 38 to the guide wire 44 which, in turn, is fixed to the first implant segment 36, the fixation mechanism 46 can be said to fix the implant segment 36 to the second implant segment 38 via a threaded engagement.

While the first and second locking members 64 and 66 have been constructed in accordance with one embodiment, it is envisioned that the locking members 64 and 66 can be constructed in accordance with any suitable alternative embodiment as desired. For instance either or both of the locking members 64 and 66 can be configured as a locking pin that extends through a respective one of the implant segments and the guide wire 44, thereby fixing the respective one of the implant segments to the guide wire 44. As another example, either or both of the locking members 64 and 66 can be configured as a set screw that is threadedly driven through a channel of a respective one of the implant segments in a direction toward the corresponding central axis, and compresses against the guide wire 44. Thus, it will be appreciated that the first and second locking member 44 and 46 can be any suitably constructed locking member unless otherwise specified.

Once the locking members 64 and 66 are secured in place, the guide wire 44 can be cut at a location adjacent and proximal with respect to the locking members 64 and 66. Because the guide wire 44 have a gauge that is substantially less than conventional trans-iliac bars, a simple cutting implement can cut the guide wire 44, as opposed to larger more robust cutting instruments that were required to cut the thicker trans-iliac bars. In this regard, it is appreciated that the anatomical loads are absorbed by the first and second implant segments 36 and 38, while the guide wire 44 assists in fixation of the first and second implant segments 36 and 38 with respect to movement away from and/or toward each other. The guide wire 44 can thus have a thickness substantially less than that of conventional trans-iliac bars. For instance, the guide wire can have any thickness as desired, for instance between 0.5 mm and 3.0 mm.

Referring now to FIGS. 2 and 5A-5D, at least one of the implants 32 can be constructed in accordance with an alternative embodiment. For instance, a bone fixation implant 132 can be configured to be implanted into the first and second bone locations 31a and 31b of a patient's body. As described above with respect to the implant 32, the implant 132 illustrated in FIGS. 5A-5D can stabilize the first and second ilium bones 33a and 33b with respect to movement relative to each other while or without compressing the first and second ilium bones 33a and 33b toward each other. The bone fixation implant 132 can include the first and second implant segments 36 and 38, having the first and second shafts 40 and 42, respectively, and the first and second abutment surfaces 52 and 58, respectively, as described above. Further, the bone fixation implant can include a fixation mechanism 146 that, in turn, can include at least one locking member 164 that is configured to prevent at least one of the first and second shafts 40 and 42 from translating away from the other of the first and second shafts 40 and 42 as described above. Further, it will be appreciated that the locking member 164 does not extend through the implant from the first proximal end 40a to the second proximal end 42a.

As illustrated in FIGS. 5A-5D, the locking member 164 can be configured as a fixation member 186 that is configured to fix the first shaft 40 to the second shaft 42 with respect to movement away from each other. The fixation member 186 has a fixation head 188 and a fixation shaft 190 that extends from the fixation head 188. The fixation shaft 190 is sized and configured to be inserted through the first proximal end 40a of the first shaft 40 in the first direction, through at least a portion of the first channel 56 and into the second channel 62. The fixation shaft 190 is configured to attach to the second shaft 42 in the second channel 62, thereby fixing the first shaft 40 to the second shaft 42. The fixation member 186 defines a channel 192 that extends through the fixation head 188 and the fixation shaft 190. The channel 192 is sized and configured to receive the guide wire 144.

The fixation member 186 defines an inner surface 187a that defines the channel 192, and an outer surface 187b opposite the inner surface 187. The outer surface 187b at the fixation shaft 190 can be threaded. Thus, the fixation shaft 190 can be said to be externally threaded. Similarly, the inner surface 57a of the second shaft 42 can be threaded. Thus, the second shaft 42 can be said to be internally threaded. Thus, the fixation member 186 is configured to threadedly mate with the second shaft 42. In particular, as described above, the outer surface 187b can be threaded and configured to threadedly mate with the inner surface 57a in the second channel 62. Accordingly, the fixation shaft 190 can be configured to mate with the second shaft 42 in the second channel 62. For instance, the externally threaded surface of the fixation shaft 190 is configured to mate with the threaded inner surface 57a. The fixation member 186 can be threadedly advanced in the second channel 62 until the fixation head 188 abuts the first shaft 40. For instance, the fixation member 186 can be threadedly advanced in the second channel 62 until the fixation head 188 abuts the first proximal end 40a.

Because the fixation mechanism 146, and in particular the fixation member 186 is configured to threadedly mate with the second implant segment 38 and is configured to be fixed to the first implant segment 36, the fixation mechanism 146 can be said to fix the first implant segment 36 to the second implant segment 38 via a threaded engagement. Further, because the fixation mechanism 146, and in particular the fixation member 186 can be configured to threadedly mate with the first implant segment 36 and is further configured to be fixed to the second implant segment 36, the fixation mechanism 146 can be said to fix the first implant segment 36 to the second implant segment 38 via a threaded engagement.

As illustrated in FIG. 5D, at least a portion of the outer surface 57b of the second can define a non-circular cross-section along a plane that is normal to the first direction. Accordingly, the outer surface 57b can define a keyed surface 194. The inner surface 47a can define a complementary keyed surface as desired that mates with the keyed surface 194 so as to prevent the second shaft 42 from rotating in the first channel 56 of the first shaft 40. Alternatively or additionally, the first implant segment 36 can define at least one aperture 196 such as a pair of apertures 196 that extend through the first shaft 40 from the outer surface 47b to the inner surface 47a, such that the apertures are open to the first channel 56. The apertures 196 can be located proximate to the first distal end 40b, or otherwise positioned as desired. The second shaft 42 can be oriented in the first channel 56 such that the apertures 196 are disposed adjacent the keyed surface 194. The first implant segment 36 can further define at least one locking pin such as a pair of locking pins, which can be configured as set screws, sized and configured to be inserted into the apertures 196. For instance, the apertures 196 can be threaded or otherwise sized to receive the respective locking pin such that the locking pin applies a compressive force against the fixation shaft 190 so as to retain the second shaft 42 in the first channel 56.

As described above, the first shaft 40 can define an aperture that extends through the first proximal end 40a in the first direction. The aperture can, for instance, be defined by the first channel 56 that extends through the first shaft 40 from the first proximal end 40a to the first distal end 40b. Accordingly, the inner surface 47a of the first shaft 40 that defines the second channel 62 can further define the aperture. In one example, the fixation head 188 is sized to bias the first implant segment 36 in the first direction as the fixation shaft 190 advances along the second shaft 42 in the first direction. For instance, the fixation head 188 can be tapered in the first direction, and can be sized to be at least partially received in the aperture, so as to bear against the inner surface 47a at the aperture as the fixation member 186 moves in the first direction relative to the first shaft 40.

The fixation member 186 can thus be advanced in the second channel 62 in the first direction until the fixation head 188 applies a compressive force to the first shaft 40 in the first direction, thereby applying compression to each of the first and second ilium bones 33a and 33b toward the other of the first and second ilium bones 33a and 33b. When the sacrum S is fractured, the compression is used to promote bone healing. Since the implant 132 has the ability to maintain the compressive force throughout bone healing, the reduction of the fracture is maintained and bone healing promoted.

In another example, the outer surface 187b of the fixation member 186 at the fixation head 188 can be threaded, and at least a portion of the inner surface 47a can be threaded. Accordingly, rotation of the fixation member 186 about the guide wire 44 with respect to the first and second shafts 40 and 42 can threadedly mate the fixation head 188 to the inner surface 47a of the first shaft 40 as the fixation shaft 190 advances in the first direction along the second shaft 42 in the second channel 62. Thus, when the sacrum S (see FIG. 2) is fractured, the fracture can be reduced with, for example, reduction forceps or any suitable alternative structure, the first and second abutment surfaces 52 and 58 can abut the first and second bone locations 31a and 31b, respectively, and the fixation member 186 can secure the first and second shafts 40 and 42 to each other so as to maintain the fracture in its reduced configuration, thereby promoting bone healing.

As described above, the sacral fixation system 30 can include a guide wire 44 that is received by the first and second channels 56 and 62 as the first and second implant segments 36 and 38 are advanced toward and through the first and second bone locations 31a and 31b, respectively. The channel 192 of the fixation member 186 can further receive the guide wire 44 as the fixation shaft 190 travels into the first channel 56 and into the second distal end 42b of the second shaft 42. The fixation head 188 can compress against the first shaft 40 in the first direction so as to fix the first shaft 40 with respect to movement away from the second shaft 42. Interference between the first abutment surface 52 and the first bone location 31a prevents the first shaft 40 from moving toward the second shaft 42. Further, when the fixation shaft 190 is attached to the second shaft 42, the second shaft 42 is prevented from translating along the fixation shaft 190 in both the second and first directions toward and away from the first shaft 40, respectively. Alternatively, the fixation head 188 can threadedly mate to the first shaft 40. Accordingly, when the fixation shaft 190 threadedly mates with the second shaft 42, the fixation member 186 prevents the first and second shafts 40 and 42 from moving both toward and away from each other. The guide wire 44 can subsequently be removed from the implant 122 along either first direction or the second direction through the first channel 56, the second channel 62, and the channel of the fixation member 186. Alternatively, the fixation head 188 can define a flexible wall that is biased to compress against the guide wire 44 by the inner surface of the first shaft 40 at the first proximal end 40a, as described above with respect to the locking cap 68.

Referring now to FIGS. 2, 6A and 6B, at least one of the implants 32 illustrated in FIG. 2 can be constructed in accordance with another alternative embodiment. For instance, a bone fixation implant 232 can be configured to stabilize the first and second bone locations 31a and 31b in in accordance with another embodiment. Thus, the bone fixation implant 232 can also be referred to as a sacral fixation implant.

The bone fixation implant can include a first implant segment 236 and a second implant segment 238. The first implant segment 236 can include a first shaft 240 that is sized to be inserted through the first bone location 31a. The first shaft 240, and thus the first implant segment 236, can define a first proximal end 240a and a first distal end 240b opposite the first proximal end 240a. When the first implant segment 236 is implanted in the first bone location 31a, the first proximal end 240a can define a lateral end, and the first distal end 240b can define a medial end. The first shaft 240 can be elongate along a first central axis between the first proximal end 240a and the first distal end 240b. At least a portion up to an entirety of the first central axis can be linear. The first shaft 240 can be cylindrical in shape, or can define any suitable alternative shape as desired.

The first implant segment 236 can include a first abutment surface that extends out from the first shaft 240. For instance, the first abutment surface can be disposed proximate to the first proximal end 240a. In one example, the first implant segment 236 can include a first abutment member that extends out from the first shaft 240. The first abutment member can be raised with respect to the first shaft 240 away from the first central axis, such that the first abutment member defines the first abutment surface. As described above with respect to FIGS. 3A-4B, the first abutment member can be monolithic with the first shaft 240. Alternatively, as described above, the first abutment member, and the corresponding first abutment surface, can be separate from the first shaft 240 and attached to the first shaft 240. For instance, the first abutment member can be in the form of a washer 254 that defines an opening 259 that is sized to receive the first shaft 240, but sized smaller than the first proximal end 240a. Accordingly, the first proximal end 240a is configured to abut a first surface 254a of the washer 254, such that a second surface 254b of the washer 254 opposite the first surface 254a defines the abutment surface.

It is recognized that the central axis of the first shaft 240 might not be normal to the outer surface of the first bone location 31a when the first shaft 240 is inserted through the first bone location 31a. Accordingly, the washer 254 can be contoured such that the second surface 254b rests against the outer surface of the first bone location 31a while the first surface 254a generally conforms to the first proximal end 240a. For instance, a first end of the washer 254 can have a first thickness in the first direction, and a second end of the washer 254 can have a second thickness in the first direction that is greater than the first thickness. The first and second ends can, for instance be disposed on opposite sides of the opening 259. Thus, the abutment surface 254b can generally conform to the respective bone location. That is, a greater portion of the abutment surface 254b can abut the bone location compared to a flat surface that rests against the bone location. It should be appreciated that the abutment surface 254b can be contoured so as to substantially conform to either or both of the first and second ilium bones 33a and 33b at the perimeter of the hole that receives the respective shafts of the implant segments. The proximal end 240a can be configured as a screw head having any suitable driving interface 265, which can be configured as a socket or the like. The driving interface 265 can be configured to interlock with a driving instrument, and is configured to receive a torsional force from the driving instrument that drives the first shaft 240 to rotate about the first central axis, or otherwise maintains the first shaft 240 rotationally stable. It is appreciated that as the first proximal end 240a is tightened against the first bone location 31a, the washer 254 can remain rotationally stationary such that the proximal end 240a does not rotate in direct contact with the first bone location 31a. Rather, the proximal end 240a rotates while in contact with the washer 254. In this regard, the washer 254 can define a fixation aperture that is configured to receive suture or other type of tether so as to fix the washer 254 to or adjacent soft tissue or bone as desired, so as to fix the position of the washer 254 and assist in stabilizing the washer 254 with respect to rotation.

The first implant segment 236 can further define a first channel 256 that extends through the first shaft 240 from the first proximal end 240a to the first distal end 240b. The first channel 256 can extend along the first central axis. Thus, the first shaft 240 can define an inner surface 247a that defines the first channel 256, and an outer surface 247b opposite the inner surface 247a. The first channel 256 is sized to receive the guide wire 244. At least a portion of the outer surface 247b can be threaded so as to mate with a second shaft 242 as will be described in more detail below. The first distal end 240b can define a tip 243 that can be serrated or otherwise define a cutting flute, such that the annular tip defines a cutting surface 245 that is configured to drill a hole into the first bone location 31a. For instance, the cutting surface 245 can be placed against the first bone location 31a and the first shaft 240 can be rotated about the first central axis so that the cutting surface 245 creates a bore hole in the first bone location 31a. Thus, the first shaft 240 can be referred to as self-drilling. As described above with respect to FIG. 2, the bone fixation implant 232 can be configured to extend through the sacrum S if desired. Accordingly, it should be appreciated, for instance when the implant 232 is to extend through the sacrum S, the cutting surface 245 can create bore hole in the sacrum S after being driven through the first bone location 31a. Alternatively, a first distal end 240b can be substantially smooth or otherwise not configured to self drill through the first bone location 31a. Thus, a drilling instrument can create the bore hole in the first bone location 31a prior to insertion of the first shaft 240 through the first bone location 31a.

With continuing reference to FIGS. 2, 6A and 6B, the second implant segment 238 can include the second shaft 242 that is sized to be inserted through the second bone location 31b. The second shaft 242, and thus the second implant segment 238, can define a second proximal end 242a and a second distal end 242b opposite the second proximal end 242a. When the second implant segment 238 is implanted in the second bone location 31b, the second proximal end 242a can define a lateral end, and the second distal end 242b can define a medial end. The second shaft 242 can be elongate along a second central axis between the second proximal end 242a and the second distal end 242b. At least a portion up to an entirety of the second central axis can be linear, and can be coincident with the first central axis when the first and second shafts 240 and 242 are secured to each other. The second shaft 242 can be cylindrical in shape, or can define any suitable alternative shape as desired.

The second implant segment 238 can include a second abutment surface that extends out from the second shaft 242. For instance, the second abutment surface can be disposed proximate to the second proximal end 242a. In one example, the second implant segment 238 can include a second abutment member that extends out from the second shaft 242. The second abutment member can be raised with respect to the second shaft 242 away from the second central axis, such that the second abutment member defines the second abutment surface. As described above with respect to FIGS. 3A-4B, the second abutment member can be monolithic with the second shaft 242. Alternatively, as described above, the second abutment member, and the corresponding second abutment surface, can be separate from the second shaft 242 and attached to the second shaft 242. For instance, the second abutment member can be in the form of the washer 254, as described above. Thus, the first implant segment 236 can include a first washer 254, and the second implant segment 238 can include a second washer 254. The second proximal end 242a is configured to abut the first side 254a of the second washer 254, such that the second side 254b of the second washer 254 defines the abutment surface.

It is recognized that the central axis of the second shaft 242 might not be normal to the outer surface of the second bone location 31b when the second shaft 242 is inserted through the second bone location 31b. Accordingly, the second washer 254 can be contoured such that the second side 254b rests against the outer surface of the second bone location 31b while the first side 254a generally conforms to the second proximal end 242a. The second proximal end 242a can be configured as a screw head having any suitable driving interface 267, which can be configured as a socket or the like. The second driving interface 267 can be configured to interlock with a driving instrument, and is configured to receive a torsional force from the driving instrument that either drives the second shaft 242 to rotate about the central axis or maintains the second shaft 242 rotationally stable. It is appreciated that as the first proximal end 240a is tightened against the first bone location 31a, the washer 254 can remain rotationally stationary such that the second proximal end 242a does not rotate in direct contact with the first bone location 31a. In this regard, the second washer 254 can define a fixation aperture that is configured to receive suture or other type of tether so as to fix the second washer 254 to adjacent soft tissue or bone as desired, so as to fix the position of the second washer 254 and assist in stabilizing the second washer 254 with respect to rotation.

The second implant segment 238 can further define a second channel 262 that extends through the second shaft 242 from the second proximal end 242a to the second distal end 242b. The second channel 262 can extend along the second central axis. Thus, the second shaft 242 can define a second inner surface 257a that defines the second channel 262, and a second outer surface 257b opposite the second inner surface 257a. The second channel 262 is sized to receive the guide wire 244. At least a portion of the second inner surface 257a can be threaded so as to threadedly mate with the first outer surface 247b of the first shaft 240, as will be described in more detail below. The second distal end 242b can define a tip 253 that can be serrated or otherwise define a cutting flute, such that the annular tip defines a second cutting surface 255 that is configured to drill a hole into the second bone location 31b. For instance, the second cutting surface 255 can be placed against the second bone location 31b and the second shaft 242 can be rotated about the second central axis so that the second cutting surface 255 creates a bore hole in the second bone location 31b. Thus, the second shaft 242 can be referred to as self-drilling. As described above with respect to FIG. 2, the bone fixation implant 232 can be configured to extend through the sacrum S if desired. Accordingly, it should be appreciated, for instance when the implant 232 is to extend through the sacrum S, the second cutting surface 255 can create bore hole in the sacrum S after being driven through the second bone location 31b. Alternatively, the second distal end 242b can be substantially smooth or otherwise not configured to self drill through the first bone location 31a. Thus, a drilling instrument can create the bore hole in the second bone location 31b prior to insertion of the second shaft 242 through the second bone location 31b.

As described above, at least a portion of the first outer surface 247b of the first shaft 240 can be threaded. Similarly, at least a portion of the second inner surface 257a of the second shaft 242 can be threaded. Thus, at least one of the first and second shafts 240 and 242 can be rotated with respect to the other so as to threadedly mate the first shaft 240 with the second shaft 242 in the second channel 262. It is appreciated that the first shaft 240 can be threadedly advanced in the second channel 262, thereby applying compression to each of the first and second ilium bones 33a and 33b toward the other of the first and second ilium bones 33a and 33b.

Referring now to FIGS. 2 and 7A-C, and as described above, the sacral fixation system 30 can include a drilling instrument configured to create the bore holes in either or both of the first and second bone locations 31a and 31b. The sacral fixation system 30 can further include a targeting device 34 that can be configured as an alignment guide 300 configured to guide the guide wire 44 through the first and second bone locations 31a and 31b. The alignment guide 300 can include a support base 302, and a positionally adjustable arm 304. The alignment guide 300 can further include an elongate guide member 306 that defines a proximal end 306a and a distal end 306b spaced from the proximal end along a central axis, that is configured to be coincident with the first and second central axes of the implant segments described above. The alignment guide 300 can define a channel 307 that extends through the guide member 306 from the proximal end 306a to the distal end 306b. The central axis of the guide member 306 can define the central axis of the channel 307. The guide member 306 includes a radio opaque marker 308 at the proximal end 306a. For instance, the radio-opaque marker 308 can be configured as an annular ring that receives the proximal end 306a. The guide member 306 can further include a radio-opaque tip 310 that extends from the distal end 306b. The channel 307 can further extend through the tip 310 and the marker 308. The tip 310 can include one or more teeth 311 configured to embed into either or both of the first and second bone locations 31a and 31b. The guide member 306 can be supported by the adjustable arm 304 so as to be positionally adjustable, as will now be described.

In particular, it is recognized that it is desirable for the central axis of the guide member 306 to be aligned with the first and second bone locations 31a and 31b, such that the bore holes through either or both of the first and second bone locations 31a and 31b are properly oriented and positioned. Thus, the guide member 306 is configured to provide an indication as to whether the central axis is aligned with the first and second bone locations 31a and 31b on a radiographic image 312. The radiographic image, for instance, can be an X-Ray. In this regard, it is recognized that a visual inspection of the tip 310 might initially appear to be aligned with the first and second bone locations 31a and 31b, even though the central axis of the guide member 306 is not in alignment with the first and second bone locations 31a and 31b. The radio-opaque marker 308 and the radio-opaque tip 310 are configured to be disposed in a predetermined position with respect to each other in the radiographic image 312, indicating that the radio-opaque marker 308 and the radio-opaque tip 310 are aligned with each other. Accordingly, when the radio-opaque marker 308 and the radio-opaque tip 310 are aligned with each other on the radiographic image 312, and the channel 307 is aligned with each of the first and second bone locations 31a and 31b, then it can be concluded that the central axis of the guide member 306 is aligned with the first and second bone locations 31a and 31b. For instance, the predetermined position between the radio-opaque marker 308 and the radio-opaque tip 310 can be a concentric relationship. In one example, the tip 310 can be concentrically disposed within the radio-opaque marker 308.

If the radio-opaque marker 308 and the radio-opaque tip 310 are not aligned with each other on the radiographic image 312, the guide member 306 can be positionally adjusted until the radio-opaque marker 308 and the radio-opaque tip 310 are aligned with each other. If the radio-opaque marker 308 and the radio-opaque tip 310 are aligned with each other, but the central axis or channel 307 is not aligned with each of the first and second bone locations 31a and 31b, the guide member 306 can be positionally adjusted until the radio-opaque marker 308 and the radio-opaque tip 310 are aligned with each other, and the central axis or channel 307 are aligned with each of the first and second bone locations 31a and 31b. Next, the teeth 311 can be anchored in either of the first and second bone locations 31a while the guide member 306 is in the aligned configuration. The guide wire 44 can then be introduced through the channel 307 and through the first and second bone locations 31a and 31b alone or in combination with the sacrum S as desired. In this regard, it should be appreciated that the guide wire 44 can include a cutting tip configured to cut through the first and second bone locations 31a and 31b, alone or in combination with the sacrum S as desired.

Once the guide wire 44 is in place, a drill can be guided along the guide wire so as to create the bore holes in the first and second bone locations 31a and 31b, alone or in combination with the sacrum S as desired. The bore holes may be drilled with the same drill bit in a single drilling step, for instance if the maximum outer cross-sectional dimensions of the first and second shafts are substantially the same, or in separate drilling steps, which can be with different drill bits if the maximum cross-sectional dimensions of the first and second shafts are different than each other. The above steps can be repeated to produce as many bore holes in the first and second bone locations 31a and 31b as desired. The drill bit is removed leaving the bone prepared for insertion of one or more of the bone fixation implants 32. Alternatively still, as described above, either or both of the first and second implant segments 36 and 38 can be self-drilling.

The sacral fracture can be reduced prior to insertion of the one or more of the bone fixation implants 32, particularly when none of the bone fixation implants 32 are configured to achieve compression of the first and second ilium bones 33a and 33b toward each other. Alternatively or additionally, at least one of the bone fixation implants 32 can be configured to achieve compression of the first and second ilium bones 33a and 33b toward each other, as described above.

The foregoing description is provided for the purpose of explanation and is not to be construed as limiting the invention. While various embodiments have been described with reference to preferred embodiments or preferred methods, it is understood that the words which have been used herein are words of description and illustration, rather than words of limitation. Furthermore, although the embodiments have been described herein with reference to particular structure, methods, and embodiments, the invention is not intended to be limited to the particulars disclosed herein. For instance, it should be appreciated that structure and methods described in association with one embodiment are equally applicable to all other embodiments described herein unless otherwise indicated. Those skilled in the relevant art, having the benefit of the teachings of this specification, may effect numerous modifications to the invention as described herein, and changes may be made without departing from the spirit and scope of the invention, for instance as set forth by the appended claims.

The invention claimed is:

1. A sacral fixation system comprising:
   a first implant segment having a first shaft sized to be inserted through a first bone location, the first implant segment defining a first proximal end and a first distal end opposite the first proximal end, a first abutment surface that extends out from the first shaft and is configured to abut the first bone location so as to prevent further insertion of the first shaft through the first bone location, wherein the first implant segment defines a first channel that extends through the first shaft from the first proximal end to the first distal end; and a second implant segment having a second shaft sized to be inserted through a second bone location, the second implant segment defining a second proximal end and a second distal end opposite the second proximal end, a second channel that extends from the second proximal end to the second distal end, and a second abutment surface that extends out from the second shaft and is configured to abut the second bone location so as to prevent further insertion of the second shaft through the second bone location, wherein at least the second distal end is sized to be received in the first channel at a location between the first and second bone locations;

a Kirschner wire sized to extend through each of the first and second bone locations, such that the first and second channels are configured to receive the Kirschner wire as the first and second shafts are inserted through the first and second bone locations, respectively; and a first locking member configured to attach the first shaft to the Kirschner wire so as to fix the first implant segment with respect to movement away from the second implant segment, wherein the first locking member is separate from each of the first and second implant segments, and does not extend through the first and second shafts from the first proximal end to the second proximal end; and a second locking member, the second locking member configured to secure the second shaft to the Kirschner wire at least with respect to movement of the second shaft away from the first shaft, wherein the Kirschner wire is threaded, one of the first and second locking members comprises a locking nut that is internally threaded and thredable onto the Kirschner wire so as to abut a respective one of the first and second shafts, and apply a force against the respective one of the first and second shafts that urges the respective one of the first and second shafts toward the other of the first and second shafts, and the other of the first and second locking members comprises a locking cap having a flexible wall that is configured to compress against the Kirschner wire in response to a compression force applied to the flexible wall.

2. The sacral fixation system as recited in claim 1, wherein the first abutment surface is monolithic with the first shaft and the second abutment surface is monolithic with the second shaft.

3. The sacral fixation system as recited in claim 2, wherein the Kirschner wire is removable through the first channel, second channel, and the first locking member after the fixation member has fixed the first shaft to the second shaft.

4. The sacral fixation system as recited in claim 1, wherein each of the first and second distal ends are serrated so as to define respective cutting surfaces configured to drill a bore hole through the first and second bone locations, respectively.

5. The sacral fixation system as recited in claim 1, wherein at least one of the first and second abutment surfaces is defined by a washer that defines an opening extending therethrough in a first direction, the opening sized to receive a respective one of the first and second shafts, the washer having a first end having a first thickness and a second end having a second thickness greater than the first thickness, wherein the first and second ends are on opposite sides of the opening.

6. The sacral fixation system as recited in claim 1, wherein the locking cap is sized to be at least partially received in an aperture that extends through the respective at least one of the first and second proximal ends, such that an inner surface that defines the aperture is configured to apply the compression force to the flexible wall as the locking cap is inserted into the aperture, and wherein an outer surface of the flexible wall and the inner surface are threaded and configured to threadedly mate with each other when the locking cap is inserted into the aperture.

7. A sacral fixation system comprising:

a first implant segment having a first shaft sized to be inserted through a first bone location, the first implant segment defining a first proximal end and a first distal end opposite the first proximal end, a first abutment surface that extends out from the first shaft and is configured to abut the first bone location so as to prevent further insertion of the first shaft through the first bone location, wherein the first implant segment defines a first channel that extends through the first shaft from the first proximal end to the first distal end; and a second implant segment having a second shaft sized to be inserted through a second bone location, the second implant segment defining a second proximal end and a second distal end opposite the second proximal end, and a second abutment surface that extends out from the second shaft and is configured to abut the second bone location so as to prevent further insertion of the second shaft through the second bone location, wherein the second implant segment defines a second channel that extends at least into the second distal end along a direction toward the second proximal end, and at least the second distal end is sized to be received in the first channel at a location between the first and second bone locations; and a fixation member having a fixation head and a fixation shaft that extends from the fixation head, the fixation shaft configured to be inserted through the first proximal end so as to attach to the second shaft in the second channel and capture an entirety of the first implant segment between at least a portion of the fixation head and at least a portion of the fixation shaft, such that the fixation member fixes the first and second implant segments with respect to movement of the first and second implant segments away from each other, wherein the fixation member is separate from each of the first and second implant segments, and does not extend through the first and second shafts from the first proximal end to the second proximal end.

8. The sacral fixation system as recited in claim 7, wherein the second shaft defines an inner surface that defines the second channel, at least a portion of the inner surface is threaded, and at least a portion of the fixation shaft is threaded, such that the fixation shaft is configured to threadedly mate with the inner surface in the second channel.

9. The sacral fixation system as recited in claim 8, wherein the first proximal end is threaded, and the fixation head is threaded, such that the fixation head is configured to threadedly mate with the first proximal end as the fixation shaft threadedly mates with the inner surface in the second channel.

10. The sacral fixation system as recited in claim 7, wherein the second channel extends from the second proximal end to the second distal end, and the sacral fixation system further comprises a guide wire sized to extend through each of the first and second bone locations, such that the first and second channels are configured to receive the guide wire as the first and second shafts are inserted through the first and second bone locations, respectively.

11. The sacral fixation system as recited in claim 10, wherein the fixation member is cannulated such that the fixation member is configured to receive the guide wire as the fixation shaft is inserted through the first proximal end so as to attach to the second shaft in the second channel.

12. The sacral fixation system as recited in claim 7, wherein the second shaft defines an outer surface opposite the inner surface, and the outer surface defines a keyed surface configured to abut a keyed surface of the first shaft in the first channel so as to prevent the first and second channels rotating with respect to each other.

13. The sacral fixation system as recited in claim 12, wherein the first implant segment defines an aperture that extends through a wall of the first shaft into the first channel, the aperture configured to receive a locking pin that is configured to secure the first and second shafts to each other with respect to relative rotation.

14. The sacral fixation system as recited in claim 7, wherein the first abutment surface is monolithic with the first shaft and the second abutment surface is monolithic with the second shaft.

15. The sacral fixation system as recited in claim 7, wherein each of the first and second distal ends are serrated so as to define respective cutting surfaces configured to drill a bore hole through the first and second bone locations, respectively.

16. The sacral fixation system as recited in claim 7, wherein at least one of the first and second abutment surfaces is defined by a washer that defines an opening extending therethrough in a first direction, the opening sized to receive a respective one of the first and second shafts, the washer having a first end having a first thickness and a second end having a second thickness greater than the first thickness, wherein the first and second ends are on opposite sides of the opening.

17. The sacral fixation system as recited in claim 7, wherein the fixation head is configured to engage the first proximal end while the fixation shaft is attached to the second shaft in the second channel.

* * * * *